United States Patent [19]

Gravestock

[11] Patent Number: 6,110,936
[45] Date of Patent: Aug. 29, 2000

[54] 3-PHENYL-FURAN-(5H)-2-ONE AND DIHYDROFURAN-2-ONE DERIVATIVES AS ANTIBACTERIAL AGENTS

[75] Inventor: Michael Barry Gravestock, Macclesfield, United Kingdom

[73] Assignee: Zeneca Limited, London, United Kingdom

[21] Appl. No.: 09/180,475

[22] PCT Filed: Apr. 17, 1997

[86] PCT No.: PCT/GB97/01061

§ 371 Date: Jan. 19, 1999

§ 102(e) Date: Jan. 19, 1999

[87] PCT Pub. No.: WO97/43280

PCT Pub. Date: Nov. 20, 1997

[30] Foreign Application Priority Data

May 11, 1996 [GB] United Kingdom ............... 9609919

[51] Int. Cl.$^7$ .................. A61K 31/445; A61K 31/41; C07D 401/00; C07D 211/68; C07D 211/26

[52] U.S. Cl. .................. 514/315; 514/317; 514/318; 514/359; 546/187; 546/194; 546/242; 546/244; 546/246; 546/269.1

[58] Field of Search .................. 546/187, 191, 546/194, 242, 244, 246, 268.4, 268.7, 269.1; 514/247, 277, 315, 317, 318, 359

[56] References Cited

U.S. PATENT DOCUMENTS

| | | | |
|---|---|---|---|
| 4,287,351 | 9/1981 | Bourgery et al. | 548/232 |
| 4,346,102 | 8/1982 | Langlois et al. | 424/279 |
| 4,476,136 | 10/1984 | Dostert et al. | 424/272 |
| 4,705,799 | 11/1987 | Gregory | 514/376 |
| 4,942,183 | 7/1990 | Gregory et al. | 514/376 |
| 4,948,801 | 8/1990 | Carlson et al. | 514/307 |
| 4,977,173 | 12/1990 | Brittelli et al. | 514/376 |
| 5,043,443 | 8/1991 | Carlson et al. | 544/112 |
| 5,164,510 | 11/1992 | Brickner | 548/231 |
| 5,182,403 | 1/1993 | Brickner | 548/231 |
| 5,231,188 | 7/1993 | Brickner | 548/221 |
| 5,523,403 | 6/1996 | Barbachyn | 544/137 |
| 5,529,998 | 6/1996 | Habich et al. | 514/233.6 |
| 5,547,950 | 8/1996 | Hutchinson et al. | 514/252 |
| 5,565,571 | 10/1996 | Barbachyn et al. | 546/144 |
| 5,574,055 | 11/1996 | Borgulya et al. | 514/376 |
| 5,652,238 | 7/1997 | Brickner et al. | 514/235.8 |
| 5,654,428 | 8/1997 | Barbachyn et al. | 544/235 |
| 5,668,286 | 9/1997 | Yamada et al. | 546/209 |
| 5,688,792 | 11/1997 | Barbachyn et al. | 514/235.5 |
| 5,698,574 | 12/1997 | Reidl et al. | 514/376 |
| 5,719,154 | 2/1998 | Tucker et al. | 514/252 |
| 5,736,545 | 4/1998 | Gadwood et al. | 514/252 |

FOREIGN PATENT DOCUMENTS

| | | | |
|---|---|---|---|
| 24985/95 | 2/1996 | Australia | C07J 1/00 |
| 50735/96 | 10/1996 | Australia | C07D 413/00 |
| 2154024 | 1/1996 | Canada | C07D 413/04 |
| 0127902 | 12/1984 | European Pat. Off. | |
| 0184170 | 6/1986 | European Pat. Off. | |
| 0312000 | 4/1989 | European Pat. Off. | |
| 0316594 | 5/1989 | European Pat. Off. | |
| 0352781 | 1/1990 | European Pat. Off. | |
| 0 359 418 A1 | 3/1990 | European Pat. Off. | |
| 0 609 905 A1 | 8/1994 | European Pat. Off. | |
| 0657440 | 6/1995 | European Pat. Off. | |
| 0693491 | 1/1996 | European Pat. Off. | |
| 0694543 | 1/1996 | European Pat. Off. | C07D 413/04 |
| 0694544 | 1/1996 | European Pat. Off. | C07D 413/04 |
| 0738726 | 10/1996 | European Pat. Off. | C07D 417/04 |
| 2458547 | 1/1981 | France | C07D 263/16 |
| 2500450 | 8/1982 | France | C07D 263/20 |
| 2028306 | 3/1980 | United Kingdom | C07D 263/16 |
| 2 054 575 | 2/1981 | United Kingdom | C07D 263/20 |
| 2053196 | 2/1981 | United Kingdom | C07D 307/02 |
| 2094299 | 9/1982 | United Kingdom | C07D 263/20 |
| 2 141 716 | 1/1985 | United Kingdom | C07D 263/20 |
| 93/09103 | 5/1993 | WIPO | C07D 263/20 |
| 93/23384 | 11/1993 | WIPO | C07D 263/20 |
| 94/01110 | 1/1994 | WIPO | A61K 31/42 |
| 94/13649 | 6/1994 | WIPO | C07D 263/20 |
| 95/07271 | 3/1995 | WIPO | C07D 263/20 |

(List continued on next page.)

OTHER PUBLICATIONS

Medicinal Chem Research ,5–(Acetamidomethyl; . . . ), Alan D. Borthwick et al; pp. 22–27, Jan. 1996.

(List continued on next page.)

*Primary Examiner*—Alan L. Rotman
*Assistant Examiner*—Rita Desai
*Attorney, Agent, or Firm*—Schwegman, Lundberg, Woessner & Kluth, P.A.

[57] ABSTRACT

The invention concerns a compound of formula (I),

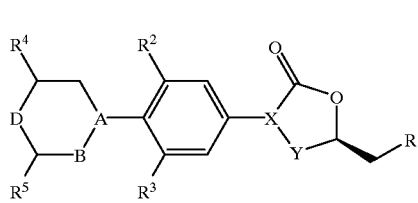

wherein, for example: $R^1$ is of the formula —NHC(=O)(1–4C) alkyl; $R^2$ and $R^3$ are hydrogen or fluoro; $R^4$ and $R^5$ are hydrogen or methyl; >A—B— is of the formula >C=CH—, >CHCH$_2$, or >C(OH)CH$_2$— (> represents two single bonds); D is O, S, SO, SO$_2$ or —NR$^7$; wherein $R^7$ is hydrogen, $R^{10}$CO—, $R^{10}$SO$_2$—, $R^aOC(R^b)$=CH(C=O)—, $R^cC$(=O)C(=O)—, $R^dN$=C($R^e$)C(=O)—, $R^fNHC(R^g)$=CHC(=O)— or $R^{14}CH(R^{13})(CH_2)_m$—; wherein $R^{10}$ is (1–6 C)alkyl [optionally substituted by, for example, hydroxy or (1–6 C)alkanoyl], $R^{11}C(O)O(1–6 C)$alkyl or $R^{12}O$—; wherein $R^{11}$ is optionally substituted (1–6 C)alkyl; $R^{12}$ is optionally substituted (1–6 C)alkyl; $R^a$, $R^b$, $R^c$, $R^d$, $R^e$, $R^f$, $R^g$ are (1–6 C)alkyl; m is 0 or 1; $R^{13}$ is cyano; $R^{14}$ is hydrogen or (1–4 C)alkyl; >X—Y— is of the formula >C'CH— or >CHCH$_2$—; and pharmaceutically acceptable salts thereof; processes for the preparation; pharmaceutical compositions containing them and their use as antibacterial agents.

13 Claims, No Drawings

FOREIGN PATENT DOCUMENTS

| | | | |
|---|---|---|---|
| 95/14684 | 6/1995 | WIPO | C07D 263/20 |
| 95/25106 | 9/1995 | WIPO | C07D 413/00 |
| 96/13502 | 5/1996 | WIPO | C07D 413/10 |
| 96/15130 | 5/1996 | WIPO | C07D 491/048 |
| 96/23788 | 8/1996 | WIPO | C07D 413/10 |
| 96/35691 | 11/1996 | WIPO | C07D 487/04 |
| 97/09328 | 3/1997 | WIPO | C07D 413/10 |
| 97/10223 | 3/1997 | WIPO | C07D 263/20 |
| 97/10235 | 3/1997 | WIPO | C07D 307/52 |
| 97/14690 | 4/1997 | WIPO | |
| 97/19089 | 5/1997 | WIPO | C07D 498/04 |
| 97/21708 | 6/1997 | WIPO | |
| 97/27188 | 7/1997 | WIPO | C07D 413/10 |
| 97/30981 | 8/1997 | WIPO | C07D 263/20 |
| 97/30995 | 8/1997 | WIPO | |
| 97/37980 | 10/1997 | WIPO | C07D 263/24 |
| 98/07708 | 2/1998 | WIPO | C07D 261/04 |

OTHER PUBLICATIONS

U.S. application No. 60/003,149, Hutchinson et al, filed Sep. 01, 1995.

U.S. application No. 60/003,837, Hester, Jr. et al., filed Sep. 15, 1995.

U.S. application No. 60/008,554, Tucker et al., filed Dec. 13, 1995.

*Abstracts: The 1996 ICAAC (Interscience Congress of Antimicrobial Agents and Chemotherapy)*, New Orleans, 41,52, 140, (Spet. 15–18, 1996).

Ashtekar, D., et al., "Oxazolidinones, a New Class of Synthetic Antituberculosis Agent: In vitro and in vivo Activities of DuP–721 Against Mycobacterium tuberculosis", *Diagn. Microbiol. Infect. Dis., 14*, 465–471, (1991).

Barbachyn, M., et al., "Identification of a Novel Oxazolidinone (U–100480) with Potent Antimycobacterial Activity", *J. Medical Chemistry, 39*, 680–685, (1996).

Barbachyn, M., et al., "Synthesis and Antibacterial Activity of New Tropone–Substituted Phenyloxazolidinone Antibacterial Agents. 1. Identification of Leads and Impotance of the Tropone Substitution Pattern.", *Bioorganic and Medicinal Chemistry Lett.. 6*, 1003–1008, (1996).

Barbachyn, M., et al., "Synthesis and Antibacterial Activity of New Tropone–Substituted Phenyloxazolidinone Antibacterial Agents. 2. Modification of the Phenyl Ring—the Potentiating Effect of Fluorine Substitution on In Vivo Activity.", *Bioorganic and Medicinal Chemistry Lett., 6*, 1009–1014, (1996).

Barry, A., et al., "In Vitro Evaluation of DuP 105 and DuP 721, Two New Oxazolidinone Antimicrobial Agents", *Antimicrobial Agents and Chemotherapy 32*, 150–152, (1988).

Borthwick, A., et al., "5–(Acetamidomethyl)–3–Aryldihydrofuran–2–ones, and 5–(Acetamidomethyl)–3–Aryltetrahydrofuran–2–ones, Two New Classes of Antibacterial Agents",*Med. Chem. Res., 6*, 22–27 (1996).

Brickner, S., et al., "Oxazolidinone Antibacterial Agents", *Current Pharmaceutical Design, 2*, 175–194, (1996).

Brickner, S., et al., "Synthesis and Antibacterial Activity of U–100592 and U–100766, Two Oxazolidinone Antibacterial Agents for the Potential Treatment of Multidrug–Resistant Gram–Positive Bacterial Infections", *J. Medical Chemistry, 39*, 673–679, (1996).

Brumfitt, W., et al., "Antibacterial Oxazolidinones: In Vitro Activity of a New Analogue, E3709", *Diagn. Microbiol, Infect. Dis., 15*, 621–625, (1992).

Brumfitt, W., et al., "In–vitro Microbiological Activities of DuP 105 and DuP 721, Novel Synthetic Oxazolidinones",*J. Antimicrobial Chemotherapy, 21*, 711–720, (1988).

Brumfitt, W., et al., "Variation in Response of Gram–Positive cocci to the Combination DuP 721 and ciprofloxacin", *J. Antimicrob. Chemotherapy, 24*, 465–466, (1989).

Daly, J., et al., "Activity and Mechanism of Action of DuP 105 and DuP 721, New Oxazolidinone Compounds", *J. Antimicrobial Chemotherapy, 21*, 721–730, (1988).

Denis, A., et al., "5–Aryl–beta,gamma Butenolide, A New Class of Antibacterial Derived from the N–Aryl Oxazolidinone DUP 721", *Bioorganic and Medicinal Chemistry Lett., 4*, 1925–1930, (1994).

Dostert, P., et al., "Structural Modifications in Oxazolidinone Series Leading to Type A or B Selective Moncamine Oxidase Inhibitors", *Int. Congress Series; Excerpta Medica, 564*, 197–208, (1982).

Eliopoulos, G., et al., "In Vitro Activities of New Oxazolidinone Antimicrobial Agents against Enterococci", *Antimicrobial Agents and Chemotherapy, 40*, 1745–1747, (1996).

Eustice, D., et al., "An Automated Pulse Labelling Method for Structure–Activity Relationship Studies with Antibacterial Oxazolidinones", *Drugs Exp. Clin. Res., 16*, 149–155, (1990).

Eustice, D., et al., "Mechanism of Action of DuP 721: Inhibition of an Early Event during Initiation of Protein Synthesis", *Antimicrobial Agents and Chemotherapy, 32*, 1218–1222, (1988).

Eustice, D., et al., "The Mechanism of Action of DuP 721, a New Antibacterial Agent: Effects on Macromolecular Synthesis", *Biochem. and Biophys. Res. Comm., 150*, 965–971, (1988).

Ford, C., et al., "In Vivo Activities of U–100592 and U–100766, Novel Oxazolidinone Antimicrobial Agents, against Experimental Bacterial Infections", *Antimicrobial Agents and Chemotherapy, 40*, 1508–1513, (1996).

Grega, K., et al., "Regioselective Metalation of Fluoroanilines. An Application to the Synthesis of Fluorinated Oxazolidinone Antibacterial Agents", *J. Org. Chem. 60*, 5255–5261, (1995).

Gregory, W., et al., "Antibacterials. Synthesis and Structure––Activity Studies of 3–Aryl–2–oxooxazolidines. 1. The "B" Group", *J. Med. Chem., 32, 1673–1681*, (1989).

Gregory, W., et al., "Antibacterials. Synthesis and Structure––Activity Studies of 3–Aryl–2–oxooxazolidines. 2. The "A" Group", *J. Med. Chem., 33*, 2569–2578, (1990).

Hutchinson, D., et al., "Piperazinyl Oxazolidinones: Structure Activity Relationshipd of a New Class of Oxazolidinone Antibacterial Agents", *Abstract: Interscience Congress of Antimicrobial Agents and Chemotherapy*, 8–14, (Sep. 17–20, 1995).

Jones, R., et al., "In Vitro Antimicrobial Activities and Spectra of U–100592 and U–100766, Two Novel Fluorinated Oxazolidinones", *Antimicrobial Agents and Chemotherapy, 40*, 720–726, (1996).

Jorgensen, J., et al., "In Vitro Activities of the Oxazolidinone Antibiotics U–100592 and U–100766 against *Staphylococcus aureus* and Coagulase–Negative Staphylococcus Species", *Antimicrobial Agents and Chemotherapy, 41*, 465–467, (Feb. 1997).

Kaatz, G., et al., "In Vitro Activities of Oxazolidinone Compounds U100592 and U100766 against *Staphylococcus aureus* and *Staphylococcus epidermis"*, *Antimicrobial Agents and Chemotherapy, 40*, 799–801, (1996).

Lin, A., et al., "The Oxazolidinone Eperezolid Binds to the 505 Ribosomal Subunit and Competes with Binding of Chloramphenicol and Lincomycin", *Antimicrobial Agents and Chemotherapy*, *41*, 2127–2131, (1997).

Lizondo, J., et al., "Linezolid U–100766", *Drugs of the Future*, *21*, 1116–1123, (1996).

Lund, J., et al., "Hypersegmented Megakaryocytes and Megakaryocytes with Multiple Separate Nuclei in Dogs Treated with PNU–100592, an Oxazolidinone Antibiotic", *Toxicologic Pathology*, *25*, 339–343, (1997).

Maple, P., et al., "Comparative in–vitro activity of vancomycin, teicoplanin, ramoplanin (formerly A16686), paldimycin, DuP 721 and DuP 105 against methicillin and gentamicin resistant *Staphylococcus aureus*", *J. Antimicrobial Chemotherapy*, *23*, 517–525, (1989).

Mason, E., et al., "In Vitro Activities of Oxazolidinones U–100592 and U–100766 against Penicillin–Resistant and Cephalosporin–Resistant Strains of *Streptococcus pneumoniae*", *Antimicrobial Agents and Chemotherapy*, *40*, 1039–1040, (1996).

Mini, E., et al., "Comparative in Vitro Activity of the New Oxazolidinones DuP 721 and DuP 105 against Staphylococci and Streptococci", *Eur. J. Clin. Microbiol. Infect. Dis.* . *8*, 256–260, (1989).

Mulazimoglu, L., et al., "In Vitro Activities of Two Novel Oxazolidinones (U100592 and U100766), a New Fluoroquinolone (Trovafloxacin), and Dalfopristin–Quinupristin against *Staphylococcus aureus* and *Staphylococcus epidermis*", *Antimicrobial Agents and Chemotherapy*, *40*, 2428–2430, (1996).

Neu, H., et al., "In Vitro Activities of Two Oxazolidinone Antimicrobial Agents, DuP 721 and DuP 105", *Antimicrobial Agents and Chemotherapy*, *32*, 580–583, (1988).

Park, C., et al., "Antibacterials. Synthesis and Structure–Activity Studies of 3–Aryl–2–oxooxazolidines. 4. Multiply–Substituted Aryl Derivatives", *J. Med. Chem.*, *53*, 1156–1165, (1992).

Ranaldi, G., et al., "Transport of the Antibacterial Agent Oxazolidin–2–One and Derivatives across Intestinal (Caco–2) and Renal (MDCK) Epithelial Cell Lines", *Antimicrobial Agents and Chemotherapy*, *40*, 652–658, (1996).

Schaadt, et al., "Serum Inhibitory Titers and Serum Bactericidal Titers for Human Subjects Receiving Multiple Doses of the Antibacterial Oxazolidinones Eperezolid and Linezolid", *Diagn. Microbiol. Infect. Dis.*, *28*, 201–204, (1997).

Schaus, S., et al., "Dynamic Kinetic Resolution of Epichlorohydrin via Enantioselective Catalytic Ring Operation with TMSN3. Practical Synthesis of Aryl Oxazolidinone Antibacterial Agents", *Tetrahedron Lett.* *37*, 7937–7940, (1996).

Scholl, J., et al., "Micellar Electrokinetic Chromatography as a Generalized Alternative to High–Performance Liquid Chromatography for Purity Determination of a Class of Investigational Antibacterial Drugs", *J. of Chromatography B*, *695*, 147–156, (1997).

Seneci, P., et al., "Synthesis and Antimicrobial Activity of Oxazolidin–2–ones and Related Heterocycles", *J. Chem. Soc. Perkin Trans. 1.* *16*, 2345–2351, (1994).

Shinabarger, D., et al., "Mechanism of Action of Oxazolidinones: Effects of Linezolid and Eperezolid on Translation Reactions", *Antimicrobial Agents and Chemotherapy*, *41*, 2132–2136, (1997).

Silverman, R., et al., "The Oxazolidinone Antibacterial Agent DuP 105 Does Not Act on Cell Wall Biosynthesis Or On A Beta–Lactamase", *Biochemical and Biophysical Research Comm.*, *195*, 1077–1080, (1993).

Slee, A., et al., "Oxazolidinones, a New Class of Synthetic Antibacterial Agents: In Vitro and In Vivo Activities of DuP 105 and DuP 721", *Antimicrobial Agents and Chemotherapy*, *31*, 1791–1797, (1987).

Spangler, S., et al., "Activities of RPR 106972 (a New Oral Streptogramin), Cefditoren (a New Oral Cephalosporin), Two New Oxazolidinones (U–100592 and U–100766), and Other Oral and Parenteral Agents against 203 Penicillin–Susceptible and –Resistant Pneumococci", *Antimicrobial Agents and Chemotherapy*, *40*, 481–484, (1996).

Takagi, H., et al., "Safety Pharmacology Evaluation of the Oxazolidinone, U–100766", *Abstract: Society of Toxicologists Annual Meeting*, 110, (1996).

Wang, C., et al., "Chiral Synthesis of DUP 721, A New Antibacterial Agent", *Tetrahedron*, *45*, 1323–1326, (1989).

Worth, S., et al., "Quality Control Guidelines for Amoxicillin, Amoxicillin–Clavulanate, Azithromycin, Piperacillin–Tazobactam, Roxithromycin, Ticarcillin, Ticarcillin–Clavulanate, Trovafloxacin (CP 99, 219), U–100592, and U–100766 for Various National Committee . . . ", *Diagn. Microbiol. Infect. Dis.* *24*, 87–91, (1996).

Zurenko, G., et al., "In Vitro Activities of U–100592 and U–100766, Novel Oxazolidinone Antibacterial Agents", *Antimicrobial Agents and Chemotherapy*, *40*, 839–845, (1996).

Zurenko, G., et al., "Oxazolidinone antibacterial agents: development of the clinical candidates eperezolid and linezolid", *Exp. Opin. Invest. Drugs*, *6*, 151–158, (1997).

3-PHENYL-FURAN-(5H)-2-ONE AND DIHYDROFURAN-2-ONE DERIVATIVES AS ANTIBACTERIAL AGENTS

This is a national stage application filed under 35 U.S.C. §371 of PCT/GB97/01061, filed Apr. 17, 1997.

The present invention relates to antibiotic compounds and in particular to antibiotic compounds containing a furanone ring. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded primarily as effective against Gram-positive pathogens because of their particularly good activity against such pathogens.

Gram-positive pathogens, for example Staphylococci, Enterococci, Streptococci and *mycobacteria,* are particularly important because of the development of resistant strains which are both difficult to treat and difficult to eradicate from the hospital environment once established. Examples of such strains are methicillin resistant *staphylococcus* (MRSA), methicillin resistant coagulase negative *staphylococci* (MRCNS), penicillin resistant *streptococcus pneumoniae* and multiply resistant *Enterococcus faecium.*

The major clinically effective antibiotic for treatment of such resistant Gram-positive pathogens is vancomycin. Vancomycin is a glycopeptide and is associated with nephrotoxicity and ototoxicity. Furthermore, and most importantly, antibacterial resistance to vancomycin and other glycopeptides is also appearing. This resistance is increasing at a steady rate rendering these agents less and less effective in the treatment of Gram-positive pathogens.

The present inventors have discovered a class of antibiotic compounds containing a furanone ring which has useful activity against Gram-positive pathogens including MRSA and MRCNS and, in particular, against various strains exhibiting resistance to vancomycin and against *E. faecium* strains resistant to both aminoglycosides and clinically used β-lactams.

We have now discovered a range of compounds that is not suggested by the art and which has good activity against a broad range of Gram-positive pathogens including organisms known to be resistant to most commonly used antibiotics. In comparison with compounds described in the art (for example Walter A. Gregory et al in J.Med.Chem. 1990, 33, 2569–2578 and Chung-Ho Park et al in J.Med.Chem. 1992, 35, 1156–1165) the compounds also possess a favourable toxicological profile.

Accordingly, there is provided a compound of the formula (I):

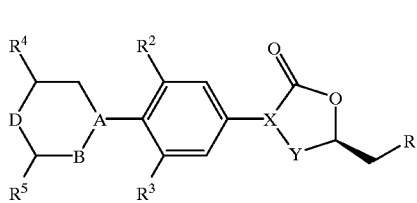

(I)

wherein:
$R^1$ is hydroxy or of the formula —NHC(=O)(1–4C)alkyl or —NHS(O)$_n$(1–4C)alkyl wherein n is 0, 1 or 2;
$R^2$ and $R^3$ are independently hydrogen or fluoro;
$R^4$ and $R^5$ are independently hydrogen or methyl
>A—B— is of the formula >C=CH—, >CHCH$_2$—, or >C(OH)CH$_2$— (> represents two single bonds);
D is O, S, SO, SO$_2$ or NR$^7$;
$R^7$ is hydrogen, cyano, 2-((1–4C)alkoxycarbonyl)ethenyl, 2-cyanoethenyl, 2-cyano-2-((1–4C)alkyl)ethenyl, 2-((1–4C)alkylaminocarbonyl)ethenyl, AR (as defined hereinbelow) or a tetrazole ring system (optionally mono-substituted in the 1- or 2-position of the tetrazole ring) wherein the tetrazole ring system is joined to the nitrogen in NR$^7$ by a ring carbon atom;
or $R^7$ is of the formula $R^{10}$CO—, $R^{10}$SO$_2$— or $R^{10}$CS—
wherein $R^{10}$ is AR (as defined hereinbelow), cyclopentyl or cyclohexyl (wherein the last two-mentioned cycloalkyl rings are optionally mono— or disubstituted by substituents independently selected from (1–4C)alkyl (including geminal disubstitution), hydroxy, (1–4C)alkoxy, (1–4C)alkylthio, acetamido, (1–4C)alkanoyl, cyano and trifluoromethyl), (1–4C)alkoxycarbonyl, hydrogen, amino, trifluoromethyl, (1–4C)alkylamino, di((1–4C)alkyl)amino, 2,3-dihydro-5-oxothiazolo-[3,2-A]pyrimidin-6-yl, 2-(2-furyl)ethenyl, 2-(2-thienyl)ethenyl, 2-phenylethenyl (wherein the phenyl substituent is optionally substituted by up to three substituents independently selected from (1–4C)alkoxy, halo and cyano), 3,4-dihydropyran-2-yl, coumal-5-yl, 5-methoxy-4-oxopyran-2-yl, N-acetylpyrrolidin-2-yl, 5-oxotetrahydrofuran-2-yl, benzopyranone or (1–10C)alkyl [wherein (1–10C)alkyl is optionally substituted by hydroxy, cyano, halo, (1–10C)alkoxy, benzyloxy, trifluoromethyl, (1–4C)alkoxy-(1–4C)alkoxy, (1–4C)alkoxy-(1–4C)alkoxy-(1–4C)alkoxy, (1–6C)alkanoyl, (1–4C)alkoxycarbonyl, amino, (1–4C)alkylamino, di((1–4C)alkyl)amino, (1–6C) alkanoylamino, (1–4C)alkoxycarbonylamino, N-( 1–4C) alkyl-N-(2–6C)alkanoylamino, (1–4C)alkylS(O)$_p$NH—, ((1–4C)alkylS(O)$_p$((1–4C)alkyl)NH—, fluoro(1–4C)alkylS(O)$_p$NH—, fluoro(1–4C)alkylS(O)$_p$((1–4C)alkyl)NH—, phosphono, (1–4C)alkoxy(hydroxy)phosphoryl, di-(1–4C) alkoxyphosphoryl, (1–4C)alkylS(O)$_q$—, phenylS(O)$_q$— (wherein the phenyl group is optionally substituted by up to three substituents independently selected from (1–4C) alkoxy, halo and cyano), or CY (as defined hereinbelow), wherein p is 1 or 2 and q is 0, 1 or 2];
or $R^{10}$ is of the formula $R^{11}$C(O)O(1–6C)alkyl wherein $R^{11}$ is an optionally substituted 5- or 6-membered heteroaryl, optionally substituted phenyl, (1–4C) alkylamino, benzyloxy-(1–4C)alkyl or optionally substituted (1–10C)alkyl;
or $R^{10}$ is of the formula $R^{12}$O— wherein $R^{12}$ is optionally substituted (1–6C)alkyl;
or $R^7$ is of the formula $R^a$OC($R^b$)=CH(C=O)—, $R^c$C(=O)C(=O)—, $R^d$N=C($R^e$)C(=O)— or $R^f$NHC($R^g$)

=CHC(=O)— wherein $R^a$ is (1–6C)alkyl, $R^b$ is hydrogen or (1–6C)alkyl, or $R^a$ and $R^b$ together form a (3–4C)alkylene chain, $R^c$ is hydrogen, (1–6C)alkyl, hydroxy(1–6C)alkyl, (1–6C)alkoxy(1–6C)alkyl, amino, (1–4C)alkylamino, di-(1–4C)alkylamino, (1–6C)alkoxy, (1–6C)alkoxy(1–6C) alkoxy, hydroxy(2–6C)alkoxy, (1–4C)alkylamino(2–6C) alkoxy, di-(1–4C)alkylamino(2–6C)alkoxy, $R^d$ is (1–6C) alkyl, hydroxy or (1–6C)alkoxy, $R^e$ is hydrogen or (1–6C) alkyl, $R^f$ is hydrogen, (1–6C)alkyl, optionally substituted phenyl or an optionally substituted 5- or 6-membered heteroaryl and $R^g$ is hydrogen or (1–6C)alkyl;

or $R^7$ is of the formula $R^{14}CH(R^{13})$ $(CH_2)_m$—wherein m is 0 or 1, $R^{13}$ is fluoro, cyano, (1–4C)alkoxy, (1–4C) alkylsulfonyl, (1–4C)alkoxycarbonyl or hydroxy, (provided that when m is 0, $R^{13}$ is not fluoro or hydroxy) and $R^{14}$ is hydrogen or (1–4C)alkyl;

wherein AR is optionally substituted phenyl, optionally substituted phenyl(1–4C)alkyl, optionally substituted 5- or 6-membered heteroaryl, optionally substituted naphthyl or an optionally substituted 5/6 or 6/6 bicyclic heteroaryl ring system, in which the bicyclic heteroaryl ring systems may be linked via an atom in either of the rings comprising the bicyclic system, and wherein the mono- and bicyclic heteroaryl ring systems are linked via a ring carbon atom;

wherein CY is a 4-, 5- or 6-membered cycloalkyl ring, a 5- or 6-membered cycloalkenyl ring, naphthoxy, thiophen-2-yl, indol-1-yl, indol-3-yl, pyrimidin-2-ylthio, 1,4-benzodioxan-6-yl, sulfolan-3-yl, pyridin-2-yl; wherein any of the afore-mentioned ring systems in CY may be optionally substituted by up to three substituents independently selected from halo, (1–4C)alkyl (including geminal disubstitution when CY is a cycloalkyl or cycloalkenyl ring), acyl, oxo and nitro-(1–4C)alkyl;

>X—Y— is of the formula >C=CH— or >CHCH$_2$—;

and pharmaceutically-acceptable salts thereof.

In this specification a '5- or 6-membered heteroaryl' and 'heteroaryl (monocyclic) ring' means a 5- or 6-membered aryl ring wherein 1, 2 or 3 of the ring atoms are selected from nitrogen, oxygen and sulfur. Particular examples of 5- or 6-membered heteroaryl ring systems are furan, pyrrole, pyrazole, imidazole, triazole, pyrimidine, pyridazine, pyridine, isoxazole, oxazole, isothiazole, thiazole and thiophene.

In this specification a '5/6 or 6/6 bicyclic heteroaryl ring system' and 'heteroaryl (bicyclic) ring' means an aromatic bicyclic ring system comprising a 6-membered ring fused to either a 5 membered ring or another 6 membered ring, the bicyclic ring system containing 1 to 4 heteroatoms selected from nitrogen, oxygen and sulfur. Particular examples of 5/6 and 6/6 bicyclic ring systems are indole, benzofuran, benzoimidazole, benzothiophene, benzisothiazole, benzoxazole, benzisoxazole, pyridoimidazole, pyrimidoimidazole, quinoline, quinoxaline, quinazoline, phthalazine, cinnoline and naphthyridine.

In this specification a '4-, 5- or 6-membered cycloalkyl ring' means a cyclobutyl, cyclopentyl or cyclohexyl ring; and a '5- or 6-membered cycloalkenyl ring' a means cyclpentenyl or cyclohexenyl ring.

In this specification the term 'alkyl' includes straight chained and branched structures. For example, (1–6C)alkyl includes propyl, isopropyl and tert-butyl. However, references to individual alkyl groups such as "propyl" are specific for the straight chained version only, and references to individual branched chain alkyl groups such as "isopropyl" are specific for the branched chain version only. A similar convention applies to other radicals, for example halo(1–4C) alkyl includes 1-bromoethyl and 2-bromoethyl.

Particular optional substituents for alkyl, phenyl (and phenyl containing moieties) and naphthyl groups and ring carbon atoms in heteroaryl (mono or bicyclic) rings in $R^{11}$, $R^{12}$, $R^i$ and AR include halo, (1–4C)alkyl, hydroxy, nitro, carbamoyl, (1–4C)alkylcarbamoyl, di-((1–4C)alkyl) carbamoyl, cyano, trifluoromethyl, trifluoromethoxy, amino, (1–4C)alkylamino, di((1–4C)alkyl)amino, (1–4C)alkyl $S(O)_q$—, (wherein q is 0, 1 or 2), carboxy, (1-1–4C) alkoxycarbonyl, (2–4C)alkenyl, (2–4C)alkynyl, (1–4C) alkanoyl, (1–4C)alkoxy, (1–4C)alkanoylamino, benzoylamino, benzoyl, phenyl (optionally substituted by up to three substituents selected from halo, (1–4C)alkoxy or cyano), furan, pyrrole, pyrazole, imidazole, triazole, pyrimidine, pyridazine, pyridine, isoxazole, oxazole, isothiazole, thiazole, thiophene, hydroxyimino(1–4C)alkyl, (1–4C)alkoxyimino(1–4C)alkyl, hydroxy-(1–4C)alkyl, halo-(1–4C)alkyl, nitro(1–4C)alkyl, amino(1 4C)alkyl, cyano(1–4C)alkyl, (1–4C)alkanesulfonamido, aminosulfonyl, (1–4C)alkylaminosulfonyl and di-((1–4C) alkyl)aminosulfonyl. The phenyl and naphthyl groups and heteroaryl (mono- or bicyclic) rings in $R^{11}$, $R^i$ and AR may be mono- or disubstituted on ring carbon atoms with substituents independently selected from the above list of particular optional substituents.

Particular optional substituents for ring nitrogen atoms when $R^-$ is tetrazole, in heteroaryl groups in $R^{11}$, $R^{12}$, $R^f$ and AR, and in the nitrogen-containing rings in CY, which can be substituted without becoming quaternised include (1–4C)alkyl, (2–4C)alkenyl, (2–4C)alkynyl and (1–4C) alkanoyl.

Examples of halo groups include fluoro, chloro and bromo; examples of (1–4C)alkyl, include methyl, ethyl, and propyl and isopropyl; examples of (1–6C)alkyl include methyl, ethyl, propyl, isopropyl, pentyl and hexyl; examples of (1–10C)alkyl include methyl, ethyl, propyl, isopropyl, pentyl, hexyl, heptyl, octyl and nonyl; examples of (1–4C) alkylamino include methylamino, ethylamino and propylamino; examples of di-((1–4C)alkyl)amino include dimethylamino, N-ethyl-N-methylamino, diethylamino, N-methyl-N-propylamino and dipropylamino; examples of (1–4C)alkylS(O)$_q$— wherein q is 0, 1 or 2 include methylthio, ethylthio, methylsulfinyl, ethylsulfinyl, methylsulfonyl and ethylsulfonyl; examples of (1–4C) alkanesulfonyloxy include methylsulfonyloxy, ethylsulfonyloxy and propylsulfonyloxy; examples of (1–4C)alkylthio include methylthio and ethylthio; examples of (1–4C) alkylsulfonyl include methylsulfonyl and ethylsulfonyl; examples of (1–4C)alkylaminocarbonyloxy include methylaminocarbonyloxy and ethylaminocarbonyloxy; examples of (1–4C)alkanoylamino-(1–4C)alkyl include formamidomethyl, acetamidomethyl and acetamidoethyl; examples of (1–6C)alkoxy-(1–6C)alkyl include methoxymethyl, ethoxymethyl and 2-methoxyethyl; examples of (1–4C)alkoxycarbonyl include methoxycarbonyl, ethoxycarbonyl and propoxycarbonyl; examples of (2–4C)alkanoyloxy include acetyloxy and propionyloxy; examples of (1–4C)alkoxy include methoxy, ethoxy and propoxy; examples of (1–6C)alkoxy and (1–10C)alkoxy include methoxy, ethoxy, propoxy and pentoxy; examples of hydroxy-(2–6C)alkoxy include 2-hydroxyethoxy and 3-hydroxypropoxy; examples of (1–4C)alkylamino-(2–6C)alkoxy include 2-methylaminoethoxy and 2-ethylaminoethoxy; examples of di-(1–4C)alkylamino-(2–6C)alkoxy include 2-dimethylaminoethoxy and 2-diethylaminoethoxy; examples of (1–4C)alkoxy-(1–4C)alkoxy and (1–6C) alkoxy-(1–6C)alkoxy include methoxymethoxy, 2-methoxyethoxy, 2-ethoxyethoxy and 3-methoxypropoxy; examples of (1–4C)alkoxy-( l4C)alkoxy-(1–4C)alkoxy include 2-(methoxymethoxy)ethoxy, 2-(2-methoxyethoxy) ethoxy; 3-(2-methoxyethoxy)propoxy and 2-(2-ethoxyethoxy)ethoxy; examples of (1–4C)alkanoylamino and (1–6C)alkanoylamino include formamido, acetamido and propionylamino; examples of (1–4C) alkoxycarbonylamino include methoxycarbonylamino and ethoxycarbonylamino; examples of N-(1–4C)alkyl-N-(1–6C)alkanoylamino include N-methylacetamido, N-ethylacetamido and N-methylpropionamido; examples of (l4C)alkylS(O)$_p$NH— wherein p is 1 or 2 include ethylsulfinylamino, methylsulfonylamino, ethylsulfinylamino and ethylsulfonylamino; examples of (1–4C)alkylS(O)$_p$((1–4C)alkyl)NH— wherein p is 1 or 2 include methylsulfinylmethylamino, methylsulfonylmethylamino, 2-(ethylsulfinyl)ethylamino and 2-(ethylsulfonyl)ethylamino; examples of fluoro(1–4C)alkylS(O)$_p$NH— wherein p is 1 or 2 include trifluoromethylsulfinylamino and trifluoromethylsulfonylamino; examples of fluoro(1–4C)alkylS(O)$_p$((1–4C)alkyl)NH— wherein p is 1 or 2 include trifluoromethylsulfinylmethylamino and trifluoromethylsulfonylmethylamino; examples of (1–4C)alkoxy(hydroxy)phosphoryl include methoxy(hydroxy)phosphoryl and ethoxy(hydroxy)phosphoryl; examples of di-(1–4C) alkoxyphosphoryl include di-methoxyphosphoryl, di-ethoxyphosphoryl and ethoxy(methoxy)phosphoryl; examples of 2-((1–4C)alkoxycarbonyl)ethenyl include 2-(methoxycarbonyl)ethenyl and 2-(ethoxycarbonyl) ethenyl; examples of 2-cyano-2-((1–4C)alkyl)ethenyl include 2-cyano-2-methylethenyl and 2-cyano-2-ethylethenyl; examples of 2-((1–4C)alkylaminocarbonyl) ethenyl include 2-(methylaminocarbonyl)ethenyl and 2-(ethylaminocarbonyl)ethenyl; examples of benzyloxy (l4C)alkyl include benzyloxymethyl and benzyloxyethyl; examples of phenyl(1–4C)alkyl include benzyl and phenethyl; examples of phenylS(O)$_q$ wherein q is 0, 1 or 2 are phenylthio, phenylsulfinyl and phenylsulfonyl respectively; examples of (1–4C)alkylcarbamoyl include methylcarbamoyl and ethylcarbamoyl; examples of di((1–4C)alkyl) carbamoyl include di(methyl)carbamoyl and di(ethyl) carbamoyl; examples of a (3–4C)alkylene chain are trimethylene or tetramethylene; examples of (2–4C)alkenyl include allyl and vinyl; examples of (2–4C)alkynyl include ethynyl and 2-propynyl; examples of (1–4C)alkanoyl and (1–6C)alkanoyl include formyl, acetyl and propionyl; examples of hydroxyimino(l4C)alkyl include hydroxyiminomethyl, 2-(hydroxyimino)ethyl and 1-(hydroxyimino)ethyl; examples of (1–4C)alkoxyimino-(1–4C)alkyl include methoxyiminomethyl, ethoxyiminomethyl, 1-(methoxyimino)ethyl and 2-(methoxyimino)ethyl; examples of hydroxy(1–4C)alkyl and hydroxy(1–6C)alkyl include hydroxymethyl, 1-hydroxyethyl, 2-hydroxyethyl and 3-hydroxypropyl; examples of halo(1–4C)alkyl include, halomethyl, 1-haloethyl, 2-haloethyl, and 3-halopropyl; examples of nitro(1–4C)alkyl include nitromethyl, 1-nitroethyl, 2-nitroethyl and 3-nitropropyl; examples of amino(1–4C) alkyl include aminomethyl, I-aminoethyl, 2-aminoethyl and 3-aminopropyl; examples of cyano(1–4C)alkyl include cyanomethyl, 1-cyanoethyl, 2-cyanoethyl and 3-cyanopropyl; examples of (1–4C)alkanesulfonamido include methanesulfonamido and ethanesulfonamido; examples of (1–4C)alkylaminosulfonyl include methylaminosulfonyl and ethylaminosulfonyl; and examples of di-(l4C)alkylaminosulfonyl include dimethylaminosulfonyl, diethylaminosulfonyl and N-methyl-N-ethylaminosulfonyl.

Suitable pharmaceutically-acceptable salts include acid addition salts such as methanesulfonate, fumarate, hydrochloride, hydrobromide, citrate, maleate and salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

The compounds of the formula (I) may be administered in the form of a pro-drug which is broken down in the human or animal body to give a compound of the formula (I). Examples of pro-drugs include in-vivo hydrolysable esters of a compound of the formula (I).

An in-vivo hydrolysable ester of a compound of the formula (I) containing carboxy or hydroxy group is, for example, a pharmaceutically-acceptable ester which is hydrolysed in the human or animal body to produce the parent acid or alcohol. Suitable pharmaceutically-acceptable esters for carboxy include (1–6C)alkoxymethyl esters for example methoxymethyl, (1–6C)alkanoyloxymethyl esters for example pivaloyloxymethyl, phthalidyl esters, (3–8C) cycloalkoxycarbonyloxy(1–6C)alkyl esters for example 1-cyclohexylcarbonyloxyethyl; 1,3-dioxolen-2-onylmethyl esters for example 5-methyl-1,3-dioxolen-2-onylmethyl; and (1–6C)alkoxycarbonyloxyethyl esters for example 1-methoxycarbonyloxyethyl and may be formed at any carboxy group in the compounds of this invention.

An in-vivo hydrolysable ester of a compound of the formula (I) containing a hydroxy group includes inorganic esters such as phosphate esters and α-acyloxyalkyl ethers and related compounds which as a result of the in-vivo hydrolysis of the ester breakdown to give the parent hydroxy group. Examples of a-acyloxyalkyl ethers include acetoxymethoxy and 2,2-dimethylpropionyloxymethoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

The compounds of the present invention have a chiral centre at the 5-position of the furanone ring. The 5(R) enantiomer of formula (IA) is the pharmaceutically active enantiomer:

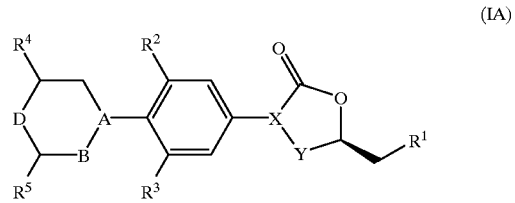

(IA)

The present invention includes the pure 5(R) enantiomer or diastereoisomer and mixtures of the 5(R) and S(S) enantiomers or diastereoisomers, for example a racemic mixture or equal mixtures of diastereoisomers. If a mixture of 5(R) and 5(S) is used, a larger amount (depending on the ratio of the enantiomers or diastereoisomers) will be required to achieve the same effects as the same weight of the 5(R) compound.

When —A—B— is of the formula >CHCH$_2$— (i.e. when the ring is a 3,4-dihydrofuranone ring) there is also a chiral centre at the 3-position. The present invention relates to both the 3R and the 3S diastereoisomers.

Furthermore, some compounds of the formula (I) may have other chiral centres, and some compounds of the formula (I) may exist as one or more regioisomers. It is to be understood that the invention encompasses all such optical, diastereo— and regio-isomers that possess antibacterial activity.

The invention relates to all tautomeric forms of the compounds of the formula (I) that possess antibacterial activity.

It is also to be understood that certain compounds of the formula (I) can exist in solvated as well as unsolvated forms such as, for example, hydrated forms. It is to be understood that the invention encompasses all such solvated forms which possess antibacterial activity.

In a preferred aspect of the invention there is provided a compound of the formula (I) wherein:

$R^1$ is hydroxy or of the formula —NHC(=O)(1–4C)alkyl or —NHS(O)$_n$(1–4C)alkyl wherein n is 0, 1 or 2;

$R^2$ and $R^3$ are independently hydrogen or fluoro;

$R^4$ and $R^5$ are independently hydrogen or methyl;

>A—B— is of the formula >C=CH—, >CHCH$_2$ or >C(OH)CH$_2$— (> represents two single bonds);

D is O, S, SO, SO$_2$ or —NR$^7$;

wherein $R^7$ is hydrogen, 2-((1–4C)alkoxycarbonyl)ethenyl, 2-((1–4C)alkylaminocarbonyl)ethenyl or optionally substituted: phenyl, phenyl(1–4C)alkyl, 5- or 6-membered heteroaryl, naphthyl or 5/6 or 6/6 bicyclic heteroaryl ring system wherein the heteroaryl ring systems are joined to the nitrogen in NR$^7$ by a ring carbon atom;

or $R^7$ is of the formula $R^{10}$CO— or $R^{10}$SO$_2$— wherein $R^{10}$ is amino, (1–4C)alkylamino, di((1–4C)alkyl)amino, or (1–6C)alkyl [wherein (1–6C)alkyl is optionally substituted by hydroxy, cyano, (1–6C) alkanoyl, amino, (1–4C)alkylamino, di-(1–4C) alkylamino, (1–6C) alkanoylamino, N-(1–4C)alkyl-N-(1–6C)alkanoylamino, (1–4C)alkylS(O)pNH—, (1–4C)alkylS(O)$_p$((1–4C)alkyl)NH—, phosphono, (1–4C)alkoxy(hydroxy)phosphoryl, di-(1–4C)alkoxyphosphoryl, or (1–4C)alkylS(O)$_p$ wherein p is 1 or 2];

or $R^{10}$ is of the formula $R^{11}$C(O)O(1–6C)alkyl wherein $R^{11}$ is optionally substituted 5- or 6-membered heteroaryl, optionally substituted phenyl or optionally substituted (1–6C)alkyl;

or $R^{10}$ is of the formula $R^{12}$O— wherein $R^{12}$ is optionally substituted (1–6C)alkyl;

or $R^7$ is of the formula $R^a$OC($R^b$)=CH(C=O)—. $R^c$C(=O)C(=O)—, $R^d$N=C($R^e$)C(=O)— or $R^f$NHC($R^g$)=CHC(=O)— wherein $R^a$ is (1–6C)alkyl, $R^b$ is hydrogen or (1–6C)alkyl or $R^a$ and $R^b$ together form a (3–4C)alkylene chain, $R^c$ is hydrogen, (1–6C)alkyl, hydroxy(1–6C)alkyl, (1–6C)alkoxy(1–6C)alkyl, amino, (1–4C)alkylamino, di-(1–4C)alkylamino, (1–6C) alkoxy, (1–6C)alkoxy(1–6C)alkoxy, hydroxy(2–6C)alkoxy, (1–4C)alkylamino(2–6C)alkoxy, di-(1–4C)alkylamino(2–6C)alkoxy, $R^d$ is (1–6C)alkyl, hydroxy or (1–6C)alkoxy, $R^e$ is hydrogen or (1–6C)alkyl, $R^f$ is (1–6C)alkyl, phenyl or a 5- or 6-membered heteroaryl and $R^g$ is hydrogen or (1–6C)alkyl;

or $R^7$ is of the formula $R^{14}$CH($R^{13}$)(CH$_2$)$_m$— wherein m is 0 or 1, $R^{13}$ is fluoro, cyano, (1–4C)alkoxy, (1–4C)alkylsulfonyl, (1–4C)alkoxycarbonyl or hydroxy; (provided that when m is 0, $R^{13}$ is not fluoro or hydroxy) and $R^{14}$ is hydrogen or (1–4C)alkyl;

>X—Y— is of the formula >C=CH— or >CHCH$_2$—;

and pharmaceutically-acceptable salts thereof.

In the above preferred aspect of the invention particular examples a '5- or 6-membered heteroaryl' and 'heteroaryl (monocyclic) ring' are imidazole, triazole, pyrimidine, pyridazine, pyridine, isoxazole,. oxazole, isothiazole, thiazole and thiophene.

Also in the above preferred aspect of the invention particular examples a '5/6 or 6/6 bicyclic heteroaryl ring system' and 'heteroaryl (bicyclic) ring' are benzofuran, benzoimidazole, benzothiophene, benzisothiazole, benzoxazole, benzisoxazole, pyridoimidazole, pyrimidoimidazole, quinoline, quinoxaline, quinazoline, phthalazine, cinnoline and naphthyridine.

Also in the above preferred aspect of the invention particular substituents for alkyl and phenyl groups and ring carbon atoms in heteroaryl (mono or bicyclic) rings in $R^7$, $R^{11}$ or $R^{12}$ include halo, (1–4C)alkyl , hydroxy, nitro, carbamoyl, (1–4C)alkylcarbamoyl, di((1–4C)alkyl) carbamoyl, cyano, trifluoromethyl, amino, (1–4C)alkylamino, di((1–4C)alkyl)amino, (1–4C)alkyl S(O)$_p$—, (wherein p is 0, 1 or 2), carboxy, (1–4C)alkoxycarbonyl, (2–4C)alkenyl, (2–4C)alkynyl, (1–4C)alkanoyl, (1–4C) alkoxy, (1–4C)alkanoylamino, benzoylamino, hydroxyimino(1–4C)alkyl, (1–4C)alkoxyimino(1–4C)alkyl, hydroxy(1–4C)alkyl, halo(1–4C)alkyl, nitro(1–4C)alkyl, amino(1–4C)alkyl, cyano(1–4C)alkyl, (1–4C)alkanesulfonamido and (1–4C)alkylaminosulfonyl.

In a further preferred aspect of the invention there is provided a compound of the formula (I) as defined in the above preferred aspect of the invention, wherein $R^{10}$ when it is (1–6C)alkyl is additionally optionally substituted with (1–6C)alkoxy and benzyloxy; and pharmaceutically-acceptable salts thereof.

Particularly preferred compounds of the invention comprise a compound of the formula (I), or a pharmaceutically-acceptable salt thereof, wherein the substituents A, B, D, X, Y and $R^1$ to $R^5$ and other optional substituents mentioned above have the values disclosed hereinbefore, or any of the following values:

(a) Preferably $R^1$ is of the formula —NHC(=O)(1–4C) alkyl. Most preferably $R^1$ is acetamido.

(b) Preferably one of $R^2$ and $R^3$ is hydrogen and the other is fluoro.

(c) Preferably >A—B— is of the formula >C=CH— or >CHCH$_2$—.

(d) Preferably $R^4$ and $R^5$ are hydrogen.

(e) Preferably D is O, S or of the formula —NR$^7$.

(f) Preferred substituents for phenyl and carbon atoms in heteroaryl (mono and bicyclic) ring systems in $R^7$ and $R^{11}$ include halo, (1–4C)alkyl, hydroxy, nitro, amino, cyano, (1–4C)alkyl S(O)p— and (1–4C)alkoxy.

(g) Preferred optional substituents for (1–6C)alkyl in $R^{11}$ are hydroxy, cyano, amino, (1–4C)alkylamino, di((1–4C)alkyl)amino, (1–4C)alkylS(O)$_p$ (wherein p is 1 or 2), carboxy, (1–4C)alkoxycarbonyl, (1–4C)alkoxy, piperazino or morpholino.

(h) Preferred optional substituents for (1–6C)alkyl in $R^{12}$ are hydroxy, (1–4C)alkoxy, cyano, amino, (1–4C)alkylamino, di((1–2C)alkyl)amino, (1–4C)alkylS(O)$_p$ (wherein p is 1 or 2).

(i) Preferably the 5/6 or 6/6 bicyclic ring system in $R^7$ is unsubstituted.

(j) Preferably 5- or 6-membered heteroaryl rings in $R^{11}$ are unsubstituted.

(k) Preferably the 5- or 6-membered heteroaryl in $R^{11}$ is pyridyl or imidazol-1-yl.

(l) Preferably $R^{12}$ is (1–6C)alkyl. Most preferably $R^{12}$ is methyl or tert-butyl.

(m) Preferably $R^{13}$ is cyano or fluoro.

(n) Preferably $R^{14}$ is hydrogen.

(o) Preferably $R^7$ is hydrogen, benzyl, pyridyl, pyrimidyl, imidazolyl, triazolyl or of the formula $R^{10}CO$—.

(p) Preferably $R^{10}$ is hydroxy(1–4C)alkyl, (l4C)alkyl, dimethylamino(l4C)alkyl, (1–4C)alkanoyloxy(1–4C)alkyl, benzyloxy(1–6C)alkyl, (1–5C)alkoxy or 2-cyanoethyl.

(q) More preferably $R^{10}$ is hydroxymethyl, methyl, dimethylaminomethyl, acetoxymethyl, methoxy, tert-butoxy or 2-cyanoethyl. More preferably $R^7$ is hydrogen, pyridyl, pyrimidyl, triazolyl, imidazolyl, benzyl, methoxycarbonyl, tert-butoxycarbonyl, hydroxyacetyl, dimethylaminoacetyl or methanesulfonyl.

(r) More preferably $R^{10}$ is hydroxymethyl, methyl, benzyloxymethyl, acetoxymethyl, methoxy or tert-butoxy. More preferably $R^7$ is hydrogen, pyridyl, pyrimidyl, triazolyl, imidazolyl, benzyl, methoxycarbonyl, tert-butoxycarbonyl, hydroxyacetyl. dimethylaminoacetyl or methanesulfonyl.

(s) Most preferably $R^{10}$ is methyl, methoxy, tert-butoxy or hydroxymethyl. Most preferably $R^7$ is hydrogen, methanesulfonyl, methoxycarbonyl, tert-butoxycarbonyl or hydroxyacetyl.

(t) Preferably XY is >C=CH—.

Therefore, especially preferred compounds are those defined in the above further preferred aspect of the invention wherein $R^1$ is of the formula —NHC(=O)(1–4C)alkyl; >A—B— is of the formula >C=CH— or >CHCH$_2$— and D is O, S or of the formula —NR$^7$; and pharmaceutically-acceptable salts thereof.

Of the above especially preferred compounds, particular especially preferred compounds of the present invention are of the formula (I) wherein $R^1$ is acetamido; >X—Y— is of the formula >C=CH—; one of $R^2$ and $R^3$ is hydrogen and the other is fluoro; >A—B— is of the formula >C=CH—; $R^4$ and $R^5$ are hydrogen; D is O, S or of the formula —NR$^7$; $R^7$ is hydrogen or of the formula $R^{10}CO$—; $R^{10}$ is hydroxy(1–4C)alkyl, (1–4C)alkanoyloxy(1–4C)alkyl or (1–5C)alkoxy; and pharmaceutically-acceptable salts thereof.

Further particularly preferred compounds of the present invention are those as defined above as particular especially preferred compounds, but with $R^2$ and $R^3$ both hydrogen; and pharmaceutically-acceptable salts thereof.

Particular compounds of the present invention are:

5R-acetamidomethyl-3-(4-[1-tert-butoxycarbonyl-1,2,5,6-tetrahydropyrid-4-yl]phenyl)dihydrofuran-2(3H)-one;

5R-acetamidomethyl-3-(4-[1,2,5,6-tetrahydropyrid-4-yl]phenyl)dihydrofuran-2(3H)-one;

5R-acetamidomethyl-3-(4-[1-methoxycarbonyl-1,2,5,6-tetrahydropyrid-4-yl]phenyl)dihydrofuran-2(3H)-one;

5R-acetamidomethyl-3-(4-[1-methylsulfonyl-1,2,5,6-tetrahydropyrid-4-yl]phenyl)dihydrofuran-2(3H)-one;

5R-acetamidomethyl-3-(4-[1-hydroxyacetyl-1,2,5,6-tetrahydropyrid-4-yl]phenyl)dihydrofuran-2(3H)-one;

5R-acetamidomethyl-3-(4-[1-tert-butoxycarbonyl— 1,2,5,6-tetrahydropyrid-4-yl]phenyl)furan-2(5H)-one;

5R-acetamidomethyl-3-(4-[1,2,5,6-tetrahydropyrid-4-yl]phenyl)furan-2(5H)-one;

5R-acetamidomethyl-3-(4-[1-methylsulfonyl-1,2,5,6-tetrahydropyrid-4-yl]phenyl)-furan-2(5H)-one;

5R-acetamidomethyl-3-(4-[1-hydroxyacetyl-1,2,5,6-tetrahydropyrid-4-yl]phenyl)-furan-2(5H)-one;

5R-acetamidomethyl-3-(4-[1-acetyloxymethylcarbonyl-1,2,5,6-tetrahydropyrid-4-yl]phenyl)furan-2(5H)-one;

5R-acetamidomethyl-3-(4-[1-dimethylaminoacetoxymethylcarbonyl-1,2,5,6-tetrahydropyrid-4-yl]phenyl)furan-2(5H)-one;

5R-acetamidomethyl-3-(4-[1-methoxyethylcarbonyloxyacetyl— 1,2,5,6-tetrahydropyrid-4-yl]phenyl)furan-2(5H)-one;

5R-acetamidomethyl-3-(4-[1-hydroxyacetyloxyacetyl—1,2,5,6-tetrahydropyrid-4-yl]phenyl)furan-2(5H)-one;

5R-acetamidomethyl-3-(4-[1-{4-pyridyl}-1,2,5,6-tetrahydropyrid-4-yl]phenyl)furan-2(5H)-one;

5R-acetamidomethyl-3-(4-[1-{2-pyridyl}-1,2,5,6-tetrahydropyrid-4-yl]phenyl)furan-2(5H)-one;

5R-acetamidomethyl-3-(4-[1-benzyloxyacetyl-1,2,5,6-tetrahydropyrid-4-yl]phenyl)furan-2(5H)-one;

5R-acetamidomethyl-3-(4-[1-{pyrimid-2-yl}-1,2,5,6-tetrahydropyrid-4-yl]phenyl)-furan-2(5H)-one;

5R-acetamidomethyl-3-(4-[2,3-dihydropyran4-yl]phenyl)furan-2(5H)-one;

5R-acetamidomethyl-3-(4-[2,3-dihydrothiopyran4-yl]phenyl)furan-2(5H)-one;

5R-acetamidomethyl-3-(3-fluoro-4-[2,3-dihydropyran-4-yl]phenyl)furan-2(5H)-one;

5R-acetamidomethyl-3-(3-fluoro-4-[2,3-dihydrothiopyran4-yl]phenyl)furan-2(5H)-one;

5R-acetamidomethyl-3-(3-fluoro-4-[1-tert-butoxycarbonyl-1,2,5,6-tetrahydropyrid4-yl]phenyl)furan-2(5H)-one;

5R-acetamidomethyl-3-(3-fluoro-4-[1,2,5,6-tetrahydropyrid-4-yl]phenyl)furan-2(5H)-one;

5R-acetamidomethyl-3-(3-fluoro-4-[1-acetyloxymethylcarbonyl-1,2,5,6-tetrahydropyrid-4-yl]phenyl)-furan-2(5H)-one;

5R-acetamidomethyl-3-(3-fluoro-4-[1-hydroxyacetyl-1,2,5, 6-tetrahydropyrid-4-yl]phenyl)furan-2(5H)-one;

or pharmaceutically-acceptable salts thereof

In a further aspect the present invention provides a process for preparing a compound of formula (I) or a pharmaceutically-acceptable salt thereof. The compounds of formula (I) may be prepared by deprotecting a compound of formula (II):

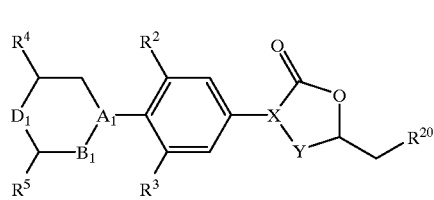

(II)

wherein $R^2$–$R^5$ and >X—Y— are as hereinabove defined, $R^{20}$ is $R^1$ or protected $R^1$, >A$_1$—B$_1$— is >A—B— or protected >C(OH)CH$_2$— and D$_1$ is D in which functional groups are optionally protected; and thereafter, if necessary, forming a pharmaceutically-acceptable salt.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (eg isopropyl, t-butyl); lower alkoxy lower alkyl groups (eg methoxymethyl, ethoxymethyl, isobutoxymethyl; lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg p-methoxybenzyl, o-nitrobenzyl, p-nitrobenzyl, benzhydryl and phthalidyl); tri(lower alkyl)silyl groups (eg trimethylsilyl and t-butyldimethylsilyl); tri(lower alkyl)silyl lower alkyl groups (eg trimethylsilylethyl); and (2–6C)alkenyl groups (eg allyl and vinylethyl).

Methods particularly appropriate for the removal of carboxyl protecting groups include for example acid—, metal— or enzymically-catalysed hydrolysis.

Examples of hydroxy protecting groups include lower alkenyl groups (eg allyl);

lower alkanoyl groups (eg acetyl); lower alkoxycarbonyl groups (eg t-butoxycarbonyl); lower alkenyloxycarbonyl groups (eg allyloxycarbonyl); aryl lower alkoxycarbonyl groups (eg benzoyloxycarbonyl, p-methoxybenzyloxycarbonyl, o-nitrobenzyloxycarbonyl, p-nitrobenzyloxycarbonyl); tri lower alkyl/arylsilyl groups (eg trimethylsilyl, t-butyldimethylsilyl, t-butyldiphenylsilyl); aryl lower alkyl groups (eg benzyl) groups; and triaryl lower alkyl groups (eg triphenylmethyl).

Examples of amino protecting groups include formyl, aralkyl groups (eg benzyl and substituted benzyl, eg p-methoxybenzyl, nitrobenzyl and 2,4-dimethoxybenzyl, and triphenylmethyl); di-p-anisylmethyl and furylmethyl groups; lower alkoxycarbonyl (eg t-butoxycarbonyl); lower alkenyloxycarbonyl (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl; trialkylsilyl (eg trimethylsilyl and t-butyldimethylsilyl); alkylidene (eg methylidene); benzylidene and substituted benzylidene groups.

Methods appropriate for removal of hydroxy and amino protecting groups include, for example, acid—, metal— or enzymically-catalysed hydrolysis, for groups such as o-nitrobenzyloxycarbonyl, photolytically and for groups such as silyl groups, fluoride.

Examples of protecting groups for amide groups include aralkoxymethyl (eg. benzyloxymethyl and substituted benzyloxymethyl); alkoxymethyl (eg. methoxymethyl and trimethylsilylethoxymethyl); tri alkyl/arylsilyl (eg. trimethylsilyl, t-butyldimethylsilyl, t-butyldiphenylsilyl); tri alkyl/arylsilyloxymethyl (eg. t-butyldimethylsilyloxymethyl, t-butyldiphenylsilyloxymethyl); 4-alkoxyphenyl (eg. 4-methoxyphenyl); 2,4-di(alkoxy)phenyl (eg. 2,4-dimethoxyphenyl); 4-alkoxybenzyl (eg. 4-methoxybenzyl); 2,4-di(alkoxy)benzyl (eg. 2,4-di(methoxy)benzyl); and alk-1-enyl (eg. allyl, but-1-enyl and substituted vinyl eg. 2-phenylvinyl).

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/silyl groups may be introduced by reacting the amide with the appropriate chloride and removing with acid, or in the case of the silyl containing groups fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid.

For further examples of protecting groups see one of the many general texts on the subject, for example, 'Protective Groups in Organic Synthesis' by Theodora Green (publisher: John Wiley & Sons).

In another aspect of the present invention the compounds of the formulae (I) and (II) and pharmaceutically-acceptable salts thereof can be prepared:

a) by modifying a substituent in or introducing a substituent into another compound of the formula (I) or (II);

b) when $R^{20}$ is of the formula —NHS(O)$_n$(1–4C)alkyl, wherein n is 1or 2, by oxidising a compound of the formula (I) or (II) wherein n is 0 or, when n is 2 by oxidising a compound of the formula (I) or (II) wherein n is 1;

c) when $R^{20}$ is of the formula —NHC(=O)(1–4C)alkyl or —NHS(O)$_n$(1–4C)alkyl, and >A$_1$—B$_1$— is >C=C—, >CHCH$_2$—, or protected >C(OH)CH$_2$— reacting a compound of the formula (III) with a compound of formula (IV):

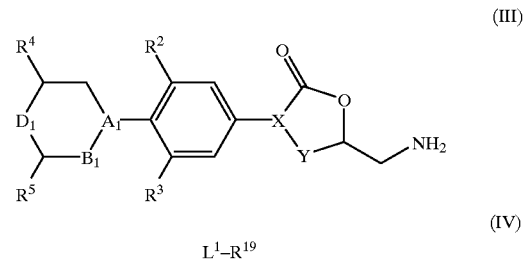

d) when $R^{20}$ is hydroxy and >X—Y— is >CHCH$_2$—:
(i) by reacting a compound of the formula (V) wherein >A$_1$—B$_1$— is >C=CH—, >CHCH$_2$— or protected >C(OH)CH$_2$— with a compound of formula (VI):

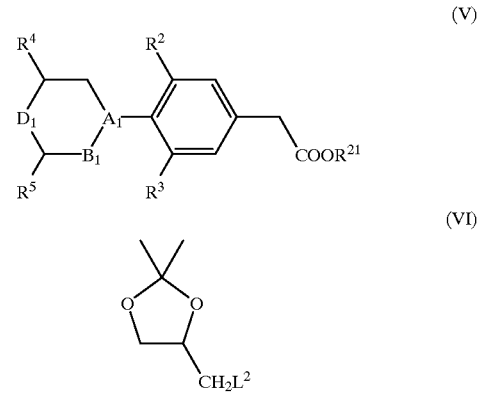

or (ii) by reacting a compound of the formula (V) with a compound of the formula (VII):

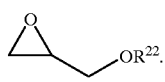

e) when >A₁—B₁— is >C=CH—, by reacting a compound of the formula (VIII) with a compound of the formula (IX):

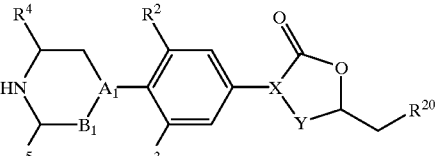

f) when >A₁—B₁— is >CHCH₂— and >X—Y— is >CHCH₂—, by catalytic hydrogenation of a compound of the formula (I) or (II) wherein >A₁—B₁— is >C=CH— and >X—Y is >CHCH₂—;

g) when >A₁—B₁— is >C=CH— and >X—Y— is >CHCH₂—, by elimination of the elements of water, or HOCOR$^{23}$, or HOSO₂R$^{24}$ from a compound of the formula (X):

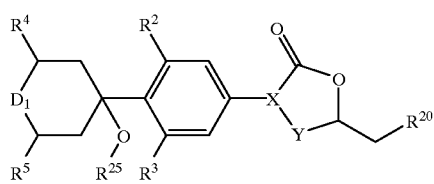

h) when >A₁—B₁— is >C=CH— and >X—Y— is >CH=CH—, by elimination of the elements of water, HOCOR$^{23}$ or HOSO₂R$^{24}$ from a compound of the formula (X) wherein >X—Y— is >C(OR$^{25}$)—CH₂—;

i) when >A₁—B₁— is >C=CH— and >X—Y— is >C=CH— by elimination of PhSOH from a compound of the formula (XI);

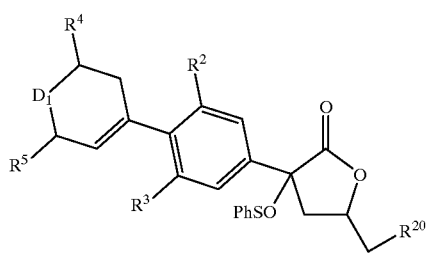

j) when D is NR$^7$ and R$^7$ is R$^{10}$CO—, R$^{10}$S(O)$_n$— or R$^{10}$CS—, by reacting a compound of the formula (XII) wherein >A₁—B₁— is >C=CH—, >CHCH₂— or protected >C(OH)CH₂—, with a compound of the formula (XIII), (XIV) or (XV) respectively wherein n is 2:

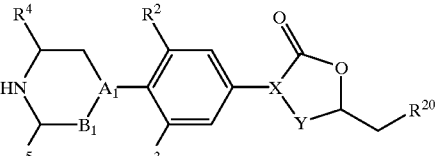

R$^{10}$COL$^4$   (XIII)

R$^{10}$SO$_n$L$^{4a}$   (XIV)

R$^{10}$CSL$^{4b}$   (XV)

k) when R$^{20}$ is of the formula —N(CO₂R$^{26}$)CO(1–4C)alkyl; from a compound of the formula (I) and (II) wherein R$^1$ or R$^{20}$ is hydroxy wherein R$^2$–R$^5$ are as hereinabove defined, R$^{19}$ is —C(=O)(1–4C)alkyl or —S(O)$_n$(1–4C)alkyl, R$^{21}$ is hydrogen or (1–6C)alkyl, R$^{22}$ is a protecting group, R$^{23}$ is (1–4C)alkyl, R$^{24}$ is an optionally substituted phenyl group and R$^{25}$ is hydrogen, (1–5C)alkanoyl or arylsulfonyl, R$^{26}$ is (1–4C)alkyl or benzyl; n is 0, 1 or 2 unless otherwise stated; L$^1$, L$^2$ and L$^{4a}$ are leaving groups, L4b is a leaving group (for example (1–4C)alkoxy), L$^3$ is an iodo or triflate leaving group, L$^4$ is hydroxy or a leaving group and Z is a trialkyltin residue, a boronate acid or ester residue or a zinc monohalide and thereafter if necessary:

i) removing any protecting groups;

ii) forming a pharmaceutically-acceptable salt.

Methods for converting substituents into other substituents are known in the art. For example an alkylthio group may be oxidised to an alkylsulfinyl or alkysulfonyl group, a cyano group reduced to an amino group, a nitro group reduced to an amino group, a hydroxy group alkylated to a methoxy group, a bromo group converted to an alkylthio group or a carbonyl group converted to a thiocarbonyl group (for example using Lawsson's reagent).

Compounds of the formula (I) or (II) wherein R$^1$ or R$^{20}$ is —NHS(O)$_n$(1–4C)alkyl can be prepared by oxidising a compound of the formula (I) or (II) with standard reagents known in the art for the oxidation of a thio group to a sulfinyl or sulfonyl group. For example, a thio group may be oxidised to a sulfinyl group with a peracid such as m-chloroperoxybenzoic acid and oxidising agents such as potassium permanganate will convert a thio group to a sulfonyl group. Compounds of the formula (I) or (II) wherein R$^1$ or R$^{20}$ is —NHS(1–4C)alkyl can be prepared by reacting compounds of the formula (III) with a reagent such as (1–4C)alkylSCl.

Standard reaction conditions for the acetylation of an amine group in a compound of the formula (III) or its conversion to a sulfonamido group are known in the art. For example, the amino group can be acetylated to give an acetamido group using the Schotten-Baumann procedure; reacting the compound of the formula (III) with acetic anhydride in aqueous sodium hydroxide and THF in a temperature range of 0° to 60° C., preferably between 0° C. and ambient temperature. Preferably the acylation is carried out in situ following the catalytic hydrogenation of a compound of the formula (IIIA) (below), by performing the hydrogenation in the presence of acetic anhydride.

A compound of the formula (III) could, for example, be converted into a compound of the formula (I) or (II) wherein $R^1$ or $R^{20}$ is (1–4C)alkylSO$_2$NH— by reacting the compound of the formula (III) with a sulfonyl chloride. For example, by reacting the compound of the formula (III) with mesyl chloride in a mild base such as pyridine.

Alternatively, compounds of the formula (I) or (II) wherein $R^1$ or $R^{20}$ is (1–4C)alkylSO$_2$NH— or (1–4C)alkylSONH— may be prepared by reacting a compound of the formula (III) with a compound of the formula (IV) wherein $L^1$ is a phthalimido group.

The compound of the formula (IV) wherein $L^1$ is phthalimido may be prepared by oxidising a compound of the formula (IVA):

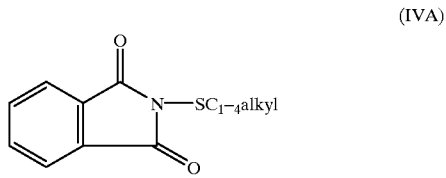

(IVA)

with standard oxidising agents known for the conversion of a thio group to a sulfinyl or sulfonyl group.

Compounds of the formula (IVA) can be prepared by reacting phthalimide with an alkylthiochloride ((1–4C)alkylSCl).

A compound of the formula (III) may be prepared by reducing a compound of the formula (IIIA):

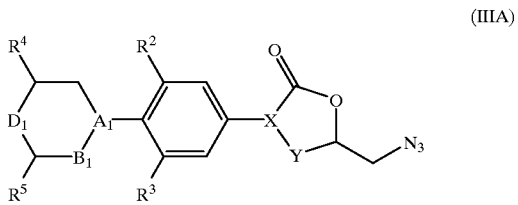

(IIIA)

wherein $R^2$–$R^5$ are as hereinabove defined, and >A$_1$—B$_1$— is >C═CH—, >CHCH$_2$— or protected >C(OH)CH$_2$—.

Suitable reducing agents include triethylamine/hydrogen sulfide, triphenylphosphine and phosphite ester. More specifically a compound of the formula (IIIA) may be converted to a compound of the formula (III) by heating it in an aprotic solvent, such as 1,2-dimethoxyethane, in the presence of P(OMe)$_3$ and subsequently in 6N aqueous hydrochloric acid. For further details on the reduction of azides to amines see U.S. Pat. No. 4,705,799. A compound of the formula (IIIA) may be reduced and converted to a compound of the formula (I) or (II) in situ using acetic anhydride in DMF.

A compound of the formula (IIIA) may be prepared by reacting a compound of the formula (IIIB):

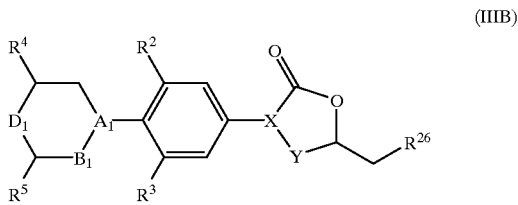

(IIIB)

wherein $R^{26}$ is mesyloxy or tosyloxy, with a source of azide. For example, by reacting (IIIB) with sodium azide in an inert solvent such as DMF in a temperature range of ambient to 100° C., normally in the region of 75° C.–85° C. A compound of the formula (IIIB) may be prepared by converting the hydroxy group in a compound of the formula (I) or (II) wherein $R^1$ or $R^{20}$ is hydroxy into a tosyloxy or mesyloxy group by standard methods known in the art. For example, by reacting the compound of the formula (I) or (II) with tosyl chloride or mesyl chloride in the presence of a mild base such as triethylamine or pyridine.

Alternatively, a compound of the formula (III) may be prepared using similar processes to those used hereinabove and hereinafter for the preparation of compounds of the formulae (I) and (II), wherein $R^{20}$ is amino.

Compounds of the formulae (V) and (VI) are conveniently reacted together in the presence of a strong base such as lithium hexamethyldisilazide or lithium diisopropylamide. The reaction is conveniently carried out in an inert solvent such as tetrahydrofuran (THF), dimethylformamide (DMF), N,N'-dimethylpropyleneurea (DMPU) or NMP in a temperature range of −78° C. to −50° C. for the deprotonation. Suitable values for $R^{21}$ include hydrogen, methyl and ethyl and suitable values for $L^2$ include iodo and tosyloxy.

The intermediate product from the alkylation is cyclised to the final product of the formula (I) or (II) wherein >X—Y— is >CHCH$_2$— and $R^1$ or $R^{20}$ is hydroxy, by heating it in aqueous acid, for example 5N hydrochloric acid, together with an organic co-solvent such as tetrahydrofuran.

Compounds of the formula (V) and (VII) are also conveniently reacted together in the presence of lithium diisopropylamide or lithium hexamethyldisilazide as above. The isolated product of this reaction may be cyclised to a compound of the formula (II) wherein >X—Y— is >CHCH$_2$— and $R^{20}$ is —OR$^{22}$ by heating this intermediate product in an aqueous acid as the solvent. When $R^{22}$ is benzyl or a similar protecting group and >A$_1$-B$_1$— is >CHCH$_2$—, —OR$^{22}$ may be deprotected by hydrogenation using methods known in the art and when >A$_1$-B$_1$— is >C═CH— by transfer hydrogenation, for example with ammonium formate.

A compound of the formula (V) is conveniently prepared by coupling a compound of the formula (VA) with a compound of the formula (IX):

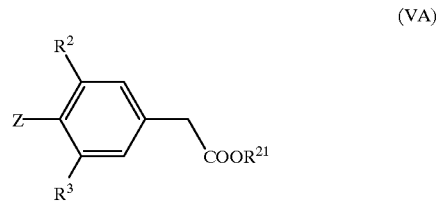

(VA)

wherein $R^2$–$R^5$, $R^{21}$·$L^3$, Z and D$_1$ are as hereinabove defined.

The reaction between compounds of the formulae (VA) and (IX), wherein Z is trialkyltin and $L^3$ is triflate is conveniently carried out in the presence of a palladium (0) catalyst such as Pd(PPh$_3$)$_4$ or Pd(dba)$_3$ in a temperature range of 0–115° C. Preferably the trialkyltin group is trimethyltin.

When Z is a boronate acid or ester, the reaction may be carried out under conditions known for the Suzuki reaction i.e. in the presence of a palladium (0) catalyst such as Pd(PPh$_3$)$_4$ or Pd(dba)$_3$, in a water-miscible organic solvent such as dimethylformamide or 1,2dimethoxyethane and in the presence of a mild base such as sodium acetate or sodium bicarbonate which is added in water. The reaction is then heated to up to 80° C. Alternatively, silver oxide may be used in place of the base, in which case the reaction may be carried out at a lower temperature. Preferably $L^3$ is iodo. Suitable boronate esters include lower alkyl and cyclic boronante esters.

The reaction between compounds of the formulae (VA) and (IX), wherein Z is a zinc monohalide is conveniently carried out in the presence of a palladium (0) catalyst such as $Pd(PPh_3)_4$ or $Pd(dba)_3$, in an inert solvent such as tetrahydrofuran, toluene or acetonitrile, in a temperature range of ambient temperature to reflux.

A compound of the formula (VA) wherein Z is trimethylstannyl may be prepared by reacting a compound of the formula (VII) wherein Z is iodo or bromo, in an inert solvent with hexamethyldistannane in the presence of a palladium (0) catalyst, or by using methods similar to those described in Patent Application No.WO9413649. Compounds of the formula (VA) wherein Z is a cyclic boronate ester as in (VB):

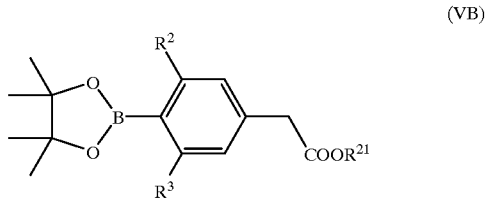

(VB)

may be prepared from a compound of the formula (VA) wherein Z is iodo or bromo, by sequential treatment with a suitable Pd catalyst such as $PdCl_2(dppf)$, potassium acetate and the pinacol ester of diboron in a polar solvent such as DMSO (for example see J.Org.Chem., 1995, 60, 7508–7510).

A compound of the formula (VA) wherein Z is a zinc monohalide may be prepared by reacting the appropriate compound of the formula (VA) wherein Z is iodo or bromo with a reactive form of zinc, such as zinc dust activated with zinc-copper couple (Tet. Lett. 1988, 5013) or with zinc halide and lithium naphthalenealide (J.O.C. 56, 1445, (1991))

A compound of the formula (IX) wherein $D_1$ is $R^{10}CON$—, S or O and $L^3$ is triflate may be prepared by treating a compound of the formula (IXA) with lithium diisopropylamide in an inert solvent such as THF, at a low temperature, for example −78° C., followed by N-phenyl triflamide (for example see methods described in Synthesis, 993–995 (1991)).

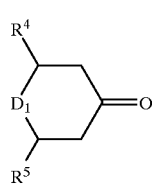

(IXA)

Alternatively, a compound of the formula (IX) wherein $L^3$ is iodo may be prepared by treating a hydrazone of a compound of the formula (IXA) with iodine in the presence of triethylamine (for example see methods detailed in Tet. Letts., 24, 1605–1608 (1983)).

Compounds of the formula (IX) and other intermediates in which $D_1$ is $NR^7$ and $R^7$ is $R^{14}CH(R^{13})(CH_2)_m$— or optionally substituted: phenyl, phenyl(1–4C)alkyl, 5- or 6-membered heteroaryl, naphthyl or 5/6 or 6/6 bicyclic heteroaryl ring system may be prepared by elaboration of the piperidone ring from the appropriate alkyl-, aryl-, heteroaryl-, arylalkyl- or heteroarylalkyl-amine. The amine is reacted with ethyl acrylate to give the corresponding diethylarylimino-β,β'-dipropionate, which can be cyclised under Dieckmann conditions to give the corresponding piperidone β-ketoester, followed by decarboxylation with heating in acid (see methods described in J.Chem.Soc., 5110–5118 (1962)).

Alternatively, a compound of the formula (IX) or other intermediate wherein $R^7$ is heteroaryl may be prepared by reacting an appropriately substituted heterocycle containing a leaving group such as chloro, bromo or iodo with the appropriate 4-piperidone at an elevated temperature, in an inert solvent and optionally with an acid trapping agent.

The reaction between compounds of the formulae (VIII) and (IX) is conveniently carried out using similar methods to those described for the reaction between compounds of the formulae (VA) and (IX), except that Z is either trialkyltin or a boronate acid or ester. The compound of the formula (VIII) may be prepared from the corresponding compound in which Z is iodo or bromo using similar methods to those described for the preparation of a compound of the formula (VA).

A compound of the formula (I) or (II) wherein $>A_1$—$B_1$— is of the formula $>CHCH_2$— may be prepared from a compound of the formula (I) or (11) wherein $>X$—$Y$— is $>C=CH$—, by catalytic hydrogenation, using a suitable catalyst such as palladium-on-carbon in an appropriate inert or acidic solvent such as acetic acid.

The dehydration of a compound of the formula (X) to give a compound of formula (I) or (II) wherein $>A_1$—$B_1$— is of the formula $>C=CH$— may be carried out using agents such as polyphosphoric acid, trifluoroacetic acid, trifluoroacetic anhydride, p-hydroxytosyl, sulfuric acid, thionyl chloride etc., in an inert solvent such as toluene, and at elevated temperatures. Suitable protection of the group $R^{20}$ may be necessary as appropriate. A compound of the formula (X) wherein $R^{20}$ is hydroxy, may be prepared by reacting a compound of the formula (VI) or (VII) with a compound of the formula (XA):

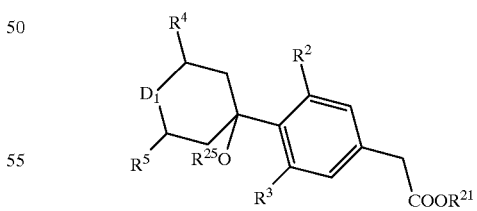

(XA)

using similar methods to those described for the reaction between compounds of the formulae (V) and (VI) or (VII). The hydroxy group $R^{20}$ may then be converted to the amine as described in the preparation of a compound of the formula (III) and subsequently to the other values of $R^{20}$.

A compound of the formula (XA) may be prepared by deprotecting a compound of the formula (XB):

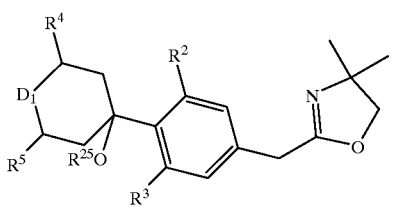

(XB)

wherein $R^2$-$R^5$ and $D_1$ are as hereinabove defined. The deprotection is conveniently carried out by refluxing it in aqueous mineral acid, such as 2N–3N hydrochloric acid.

A compound of the formula (XB) wherein $R^{25}$ is (1–5C) alkanoyl or arylsulfonyl may be prepared by acylating or sulfonylating a compound of the formula (XB) wherein $R^{25}$ is hydrogen. For example, by reacting the latter compound with the appropriate acyl halide or sulfonyl chloride in the presence of a mild base such as pyridine.

A compound of the formula (XB) wherein $R^{25}$ is hydrogen, may be prepared by reacting the Grignard or zinc/lithium agent prepared from a compound of the formula (XC):

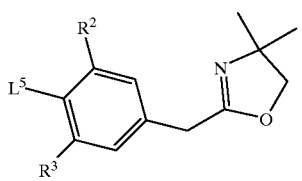

(XC)

wherein $L^5$ is iodo or bromo with a compound of the formula (IXA). Typically a Grignard or lithium organometallic species can be prepared from a compound of the formula (XC) using standard methods known in the art. The formation of the organometallic species is normally carried out in an inert solvent such as ether or tetrahydrofuran. These solutions are cooled to low temperature, for example −50° C. to −70° C., and a solution of the compound of the formula (IXA) added, followed by warming to ambient temperature to complete the reaction. More preferably a zinc organometallic species is prepared from a compound of the formula (XC) by reacting the latter compound with activated zinc metal in an inert solvent (J.Org.Chem., 56, 1445 (1996)) or Tet. Lett., 5013 (1988) and reacting the resulting solution with a solution of the compound of the formula (IXA) in a temperature range of −30° C. to 0° C.

A compound of the formula (X) wherein >X—Y— is >C(OR$^{25}$)CH$_2$— may be prepared in a similar manner to a compound of the formula (X) wherein >X—Y— is >CHCH$_2$— from an appropriate intermediate in which >X—Y— is >C(OR$^{25}$)CH$_2$—. The latter compound may be prepared by reacting the appropriate compound in which >X—Y— is >CHCH$_2$— with oxyaziridine in the presence of a strong base such as hexamethyldisilazide, in an inert organic solvent such as tetrahydrofuran to give a compound in which >X—Y— is >C(OH)CH$_2$— and subsequently acylating or sulfonylating if necessary.

A compound of the formula (XI) is usually prepared as the PhS— compound, elimination occurring on oxidation of the PhS group to PhSO— giving a compound of the formula (I) or (II) wherein >X—Y— is >C=CH—. Standard oxidising agents are known in the art. One should select an oxidising agent which is capable of oxidising the —SPh group, but not other groups in the molecule. Preferred oxidising agents for this reaction include potassium peroxymonosulfate (oxone) and sodium periodate.

Compounds in which >X—Y— is >C(SPh)CH$_2$— are conveniently prepared by reacting the appropriate compound in which >X—Y— is >CHCH$_2$— with phenyl disulfide in the presence of a base such as potassium carbonate.

These procedures for converting >X—Y— from >CHCH$_2$ into >C=CH— are not only suitable for preparing compounds of the formula (I) or (II) but also for preparing other furanone intermediates in the preparation of compounds of the formula (I) or (II).

Where an optically active form of compounds of the formula (VI) or (VII) is used in previous steps, reduction of the >X—Y— double bond will produce diastereoisomers which may be separated. Where a particular diastereoisomer is of choice, a chiral asymmetry-inducing catalyst for the reduction can be used.

Compounds of the formulae (XII) and (XIII) or (XIV) are reacted together under standard acylation or sulfonylation conditions. For example $L^4$ may be chloro and the reaction may be performed in the presence of an organic base, such as pyridine or triethylamine, in a temperature range of 0° C. to ambient temperature, in an inert organic solvent such as tetrahydrofuran or methylene chloride. Alternatively, the compound of the formula (XIII) may be replaced with acetic anhydride, in which case the reaction may be carried out in the presence of base such as sodium hydroxide under Schotten-Baumann conditions. When $L^4$ is hydroxy, compounds of the formulae (XII) and (XIII) may be reacted together under conditions known in the art for amino acid coupling. For example, the reaction may be carried out in an inert organic solvent in the presence of a diimide-coupling agent such as dicyclohexylcarbodiimide (DCCI).

Compounds of the formula (I) or (II) wherein D or $D_1$ is —NR$^7$ and R$^7$ is R$^{14}$CH(R$^{13}$)(CH$_2$)$_m$— may be prepared by introducing the appropriate group onto the nitrogen in the compound of the formula (XII). When m is 0, the compound of the formula (XII) and R$^{14}$CH(R$^{13}$)L$^5$ are conveniently reacted together under standard alkylation conditions. For example in an aprotic, solvent in the presence of an organic base such as triethylamine or pyridine, in a temperature range of 0–40° C. Suitable values for $L^5$ include halo, mesyl and tosyl. Preferably $L^5$ is chloro.

When m is 1, compounds of the formulae (XII) and R$^{14}$CH(R$^{13}$)C(=O)H may be reacted together under conditions known for the formation of an iminium salt, which can be reduced in situ. For example, iminium salt formation and reduction in situ may be carried out in a water-miscible solvent such as ethanol or tetrahydrofuran, in the presence of a reducing agent such as sodium cyanoborohydride (NaCNBH$_3$) under acidic conditions (Synthesis 135, 1975; Org. Prep. Proceed. Int. 11, 201, 1979). Alternatively the iminium salt may isolated and reduced with agents such as sodium borohydride or sodium cyanoborohydride to give the desired compound of the formula (I) or (II).

When m is 1 and R$^{13}$ is not hydroxy, fluoro or (1–4C) alkoxy, a compound of the formula (I) or (II) may be prepared by reacting a compound of the formula (XII) with a compound of the formula R$^{14}$C(R$^{13}$)=CH$_2$ under conditions suitable for the reaction known as the 'Michael addition'. For example, in an inert aprotic solvent such as tetrahydrofuran, in the presence of a base, in a temperature range of ambient temperature to 100° C.

When m is 1 and R$^{13}$ is hydroxy, the compound of the formula (XII) may be reacted with an epoxy compound which is substituted on a ring carbon by R$^{14}$. The reaction is conveniently carried out by heating the reagents together in a temperature range of 40–100° C.

A compound of the formula (I) or (II) wherein D or $D_1$ is SO or $SO_2$ may be prepared by oxidising the corresponding compound in which D or $D_1$ is S. Suitable oxidising agents for the conversion of D or $D_1$ to SO include potassium metaperiodate and peracids such as metachloroperoxybenzoic acid. Stronger oxidising agents, such as oxone may be used to convert D or $D_1$ to $SO_2$.

A compound in which $R^7$ is $R^fNHC(R^g)$=CHC(=O)— may be prepared by reacting the compound of the formula (XII) with a compound of the formula $R^gC(=O)CH_2COOalkyl$ in an inert solvent such as toluene, at elevated temperature and either in the presence of 4-dimethylaminopyridine or 4-methylbenzenesulfonic acid to give a compound in which D is of the formula $R^gC(=O)CH_2C(=O)$— and reacting the latter compound with a compound of the formula $R^fNH_2$ at elevated temperature in either toluene or acetic acid.

A compound in which $R^7$ is 2-((1–4C)alkoxycarbonyl)ethenyl may be prepared by reacting a compound of the formula (XII) with 2-((1–4C)alkoxycarbonyl)ethynyl at elevated temperature in either an alcohol or in an inert organic solvent. The compound in which $R^7$ is 2-((1–4C) alkoxycarbonyl)ethenyl may be converted to the corresponding compound in which $R^7$ is 2-((1–4C) alkylaminocarbonyl)ethenyl by reacting the former compound with the appropriate amine in an inert organic solvent at elevated temperature.

A compound in which $R^7$ is of the formula $R^aOC(R^b)$=CH(C=O)— may be prepared by reacting a compound of the formula (XII) with a compound of the formula $R^bC(=O)CH_2COOalkyl$ using similar conditions to those described for the reaction between a compound of the formula (XII) and a compound of the formula $R^gC(=O)CH_2COOalkyl$ to form a compound in which $R^7$ is of the formula $R^bC(=O)CH_2CO$— and reacting the latter compound with a halide of $R^a$, in an inert organic solvent such as THF, and in the presence of potassium carbonate.

A compound in which $R^7$ is of the formula $R^cC(=O)C(=O)$— may be prepared by reacting a compound of the formula (XII) with a compound of the formula $R^cC(=O)COCl$ in an organic solvent such as dichloromethane, in the presence of a mild base such as triethylamine and in a temperature range of 0–5° C. It is preferable to form a compound in which $R^c$ is an amino or substituted amino group by reacting a compound in which $R^c$ is an alkoxy group with the appropriate amine.

A compound in which $R^7$ is of the formula $R^dN=C(R^e)C(=O)$— may be prepared from a compound in which $R^7$ is $R^cC(=O)C(=O)$— or from a similar compound. The imino group may be introduced into the latter group by reacting it with the appropriate amine in an inert sorganic solvent, at elevated temperature and in the presence of an acid catalyst.

The group $R^7$ may be introduced into earlier intermediates in which D is NH using similar method to those described above. It is also possible to convert one $R^7$ group into another $R^7$ group as a final step in the preparation of a compound of the formula (I) or (II).

A compound of the formula (II) wherein $R^{20}$ is of the formula —N($CO_2R^{26}$)CO(1–4C)alkyl is conveniently prepared by reacting a compound of the formula (I) and (II) wherein $R^1$ or $R^{20}$ is hydroxy with an amide of the formula $HN(CO_2R^{26})CO(1-4C)alkyl$ under Mitsunobu conditions. For example, in the presence of tri-n-butylphosphine and 1,1'-(azodicarbonyl)dipiperidine in an organic solvent such as THF, and in the temperature range 0° C.– 60° C., but preferably at ambient temperature. Details of analogous Mitsunobu reactions are contained in Tsunoda et al, Tet. Letts., 34, 1639, (1993). Amides of the formula $HN(CO_2R^{26})CO(1–4C)alkyl$ may be prepared by standard procedures of organic chemistry which are within the ordinary skill of an organic chemist.

When an optically active form of a compound of the formula (I) is required, it may be obtained by carrying out one of the above procedures using an optically active starting material, or by resolution of a racemic form of the compound or intermediate using a standard procedure.

Similarly, when a pure regioisomer of a compound of the formula (a) is required, it may be obtained by carrying out one of the above procedures using a pure regioisomer as a starting material, or by resolution of a mixture of the regioisomers or intermediates using a standard procedure.

According to a further feature of the invention there is provided a compound of the formula (I), or a pharmaceutically-acceptable salt thereof, for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt thereof.

The invention also provides a compound of the formula (I), or a pharmaceutically-acceptable salt thereof, for use as a medicament; and the use of a compound of the formula (I) of the present invention, or a pharmaceutically-acceptable salt thereof, in the manufacture of a novel medicament for use in the production of an antibacterial effect in a warm blooded animal, such as man.

In order to use a compound of the formula (I) or a pharmaceutically-acceptable salt thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically-acceptable salt thereof and a pharmaceutically-acceptable diluent or carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, drops and sterile injectable aqueous or oily solutions or suspensions.

In addition to the compounds of the present invention the pharmaceutical composition of this invention may also contain or be co-administered with one or more known drugs selected from other clinically useful antibacterial agents (for example β-lactams or aminoglycosides). These may include penicillins, for example oxacillin or flucloxacillin and carbapenems, for example meropenem or imipenem, to broaden the therapeutic effectiveness against methicillin-resistant *staphylococci*. Compounds of this invention may also contain or be co-administered with bactericidal/permeability-increasing protein product (BPI) or efflux pump inhibitors to improve activity against gram negative bacteria and bacteria resistant to antimicrobial agents.

A suitable pharmaceutical composition of this invention is one suitable for oral administration in unit dosage form, for example a tablet or capsule which contains between 100 mg and 1 g of the compound of this invention.

In another aspect a pharmaceutical composition of the invention is one suitable for intravenous, subcutaneous or intramuscular injection.

Each patient may receive, for example, a daily intravenous, subcutaneous or intramuscular dose of 5 mgkg-$^1$ to 20 mgkg-$^1$ of the compound of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

Antibacterial Activity

The pharmaceutically-acceptable compounds of the present invention are useful antibacterial agents having a good spectrum of activity in vitro against standard Gram-positive organisms, which are used to screen for activity against pathogenic bacteria. Notably, the pharmaceutically-acceptable compounds of the present invention show activity against *enterococci, pneumococci* and *methicillin* resistant strains of *S. aureus* and coagulase negative *staphylococci*. The antibacterial spectrum and potency of a particular compound may be determined in a standard test system.

The antibacterial properties of the compounds of the invention may also be demonstrated in vivo in conventional tests.

The following results were obtained on a standard in vitro test system. The activity is described in terms of the minimum inhibitory concentration (MIC) determined by the agar-dilution technique with an inoculum size of $10^4$CFU/ spot.

Staphylococci were tested on agar, using an inoculum of $10^4$CFU/spot and an incubation temperature of 37° C. for 24 hours—standard test conditions for the expression of methicillin resistance.

Streptococci and *enterococci* were tested on agar supplemented with 5% defibrinated horse blood, an inoculum of $10^4$CFU/spot and an incubation temperature of 37° C. in an atmosphere of 5% carbon dioxide for 48 hours — blood is required for the growth of some of the test organisms.

| Organism | MIC (µg/ml) Example 5 |
|---|---|
| Staphylococcus aureus: | |
| Oxford | 4.0 |
| Novb. Res | 4.0 |
| MRQS | 4.0 |
| MRQR | 8.0 |
| Coagulase Negative Staphylococcis | |
| MS | 2.0 |
| MR | 4.0 |
| Streptococcus pyogenes C203 | 8.0 |

-continued

| Organism | MIC (µg/ml) Example 5 |
|---|---|
| Enterococcus faecalis | 8.0 |
| Bacillus subtilis | 4.0 |

Novb. Res = Novobiocin resistant
MRQS = methicillin resistant quinolone sensitive
MRQR = methicillin resistant quinolone resistant
MR = methicillin resistant The invention is now illustrated but not limited by the following Examples in which unless otherwise stated:

i) evaporations were carried out by rotary evaporation in vacuo and work-up procedures were carried out after removal of residual solids by filtration;

(ii) operations were carried out at ambient temperature, that is in the range 18–26° C. and in air unless otherwise stated, or unless the skilled person would otherwise work under an inert atmosphere;

(iii) column chromatography (by the flash procedure) was performed on Merck Kieselgel silica (Art. 9385) unless otherwise stated;

(iv) yields are given for illustration only and are not necessarily the maximum attainable;

(v) the end-products of the formula I generally have satisfactory microanalyses and their structures were confirmed by NMR and mass spectral techniques [proton magnetic resonance spectra were determined in DMSO-D6 unless otherwise stated using a Varian Gemini 2000 spectrometer operating at a field strength of 300 MHz, or a Bruker AM250 spectrometer operating at a field strength of 250 MHz; chemical shifts are reported in parts per million downfield from tetramethylsilane as an internal standard (δ scale) and peak multiplicities are shown thus: s, singlet; d, doublet; AB or dd, doublet of doublets; t, triplet, m, multiplet; fast-atom bombardment (FAB) mass spectral data were obtained using a Platform spectrometer (supplied by Micromass) ran in electrospray and, where appropriate, either positive ion data or negative ion data were collected];

(vi) intermediates were not generally fully characterised and purity was in general assessed by thin layer chromatographic, infra-red (IR), mass spectral (MS) or NMR analysis; and (vii) in which:

| MPLC | is medium pressure chromatography |
|---|---|
| TLC | is thin layer chromatography |
| DMSO | is dimethylsulfoxide |
| CDCl$_3$ | is deuterated chloroform |
| MS | is mass spectroscopy |
| ESP | is electrospray |
| CI | is chemical ionization |
| DMF | is N,N-dimethylformamide |
| THF | is tetrahydrofuran |
| LDA | is lithium diisopropylamide |
| TFA | is trifluoroacetic acid |
| NMP | is N-methylpyrrolidone |
| dba | is dibenzylideneacetone |
| DME | is dimethoxyethane |

REFERENCE EXAMPLE 1

4S-(2-Carboxy-2-(4-iodophenyl)ethyl)-2,2-dimethyl-(1,3)-dioxolane

To a stirred solution of 4-iodophenylacetic acid (20.96 g, 80 mM) in THF (120 ml) at −70° C. under argon, was slowly added 1.85 M lithium diisopropylamide in THF (91 ml, 168 mM). There was a moderate exotherm and an intense green colour developed as the dianion formed. The solution was warmed to ambient temperature for 15 minutes then cooled back to −70° C. A solution of 4S-iodomethyl-2,2-dimethyl-(1,3)-dioxolane (J. Med. Chem. 35, 4415 (1992)) (24.2 g, 100 mM) in THF (25 ml) was added and the solution was allowed to warm to ambient temperature and stirred for 18 hours. The mixture was quenched into ice/water and adjusted to about pH4 with dilute hydrochloric acid. This was extracted with ethyl acetate and the organic phase was washed with saturated NaCl, dried (over $MgSO_4$) and evaporated to give 4S-(2-carboxy-2-(4-iodophenyl)ethyl)-2, 2-dimethyl-(1,3)-dioxolane, which was used without purification.

REFERENCE EXAMPLE 2

5R, 3RS-5-Hydroxymethyl-3-(4-iodophenyl) dihydrofuran-2(3H)-one 4S-(2—Carboxy-2-(4-iodophenyl)ethyl)-2,2-dimethyl-(1,3)dioxolane (Reference Example 1) was dissolved in THF (150 ml), and 5N aqueous hydrochloric acid (150 ml) was added. The solution was stirred for 30 hours at ambient temperature. The mixture was extracted with ethyl acetate and the organic phase was dried ($MgSO_4$) and evaporated to give impure 5R-hydroxymethyl-3-(4-iodophenyl) dihydrofuran-2-one as an isomer mixture. Trituration with ether/ethyl acetate gave almost pure trans isomer (a sample was recrystallised from acetonitrile for NMR) (9.06 g). The remaining material was subjected to chromatography on MPLC (silica, using a 5% methanol/dichloromethane mixture as eluant) to give a pure isomer mixture after trituration with ether (8.86 g, cis:trans=18:7). Total yield=17.92 g (70%).

Trans isomer nmr: (200 MHz DMSO-D6)δ: 2.41 (m, partially obscured by DMSO); 3.61 (m, 2H); 4.06 (t, 1H); 4.65 (6 lines, 1H); 5.14 (t, 1H); 7.11 (AB, 2H); 7.70 (AB, 2H).

MS: $CI^+$ $(M+NH_4^+)$=336.
Elemental Analysis:
  Calculated for $C_{11}H_{11}IO_3$: C, 41.5; H, 3.5.
  Found: C, 40.9; H, 3.4.
  Calculated+¼$H_2O$: C, 40.9; H, 3.6.
  Cis/Trans 18:7 mixture nmr (200 MHz, DMSO-D6)δ: 2.14 (6 lines, 1H (cis)); 2.55 (m, partially obscured by DMSO, cis and trans); 2.63 (m, 2H); 4.10 (t+q, 1H) (cis and trans); 4.56 (m, 1H (cis)) merged with 4.66 (m, 1H (trans)); 5.15 (2×t, 1H); 7.13 (AB, 2H, Ar); 7.71 (AB, 2H), Ar).
  MS: $CI^+(M+NH_4)^+$=336.
Elemental Analysis:
  Calculated for $C_{11}H_{11}IO_3$: C, 41.5; H, 3.5.
  Found: C, 41.3; H, 3.5.

REFERENCE EXAMPLE 3

5R, 3RS-5-Methanesulfonyloxymethyl-3-(4-iodophenyl)dihydrofuran-2(3H)-one

To a stirred mixture of 5R, 3RS-5-hydroxymethyl-3-(4-iodophenyl)dihydrofuran-2-one (Reference Example 2) (17.45 g, 54.9 mM) and triethylamine (7.39, 73 mM, 10.24 ml) in dichloromethane (200 ml) at 0° C., was slowly added methanesulfonyl chloride (7.54 g, 66 mM, 5.10 ml). The mixture was allowed to warm to ambient temperature and stirred for 1 hour. The mixture was washed with diluted hydrochloric acid, water and saturated sodium bicarbonate. It was dried over anhydrous $Na_2SO4$ and evaporated to a crystalline mass which was triturated with ether to give 5R, 3RS-5-methanesulfonyloxymethyl-3-(4-iodophenyl) dihydrofuran-2-one. Yield=20.74 g (95%), cis:trans=2:1.

NMR (200 MHz, DMSO-D6)δ: 2.11 (m, 1H (cis)); 2.68 (m, 1 H (cis)); trans obscured by DMSO; 3.26 (2×S, 3H); 4.12 (m, 1H); 4.48 (m, 2H); 4.32 (m, 1H, (cis)); 4.46 (m, 1H (trans)) partially merged; 7.12 (AB, 2H); 7.72 (AB, 2H);

MS: $CI^+(M+NH_4)^+$=414.
Elemental Analysis:
  Calculated for $C_{12}H_{13}IO_5S$: C, 36.4; H, 3.3.
  Found: C, 36.1; H, 3.3.

REFERENCE EXAMPLE 4

5R, 3RS-5-Azidomethyl-3-(4-iodophenyl) dihydrofuran-2(3H)-one

A mixture of 5R, 3RS-5-methanesulfonyloxymethyl-3-(4-iodophenyl)dihydrofuran-2-one (Reference Example 3) (20.3 g, 51.3 mM) and $NaN_3$ (5.00 g, 76 mM) in DMSO (60 ml) was stirred at 80° C. for 2 hours. The mixture was quenched into water and the product was extracted with dichloromethane. The organic phase was washed with saturated NaCl, dried (over $MgSO_4$) and evaporated to give the title product in quantitative yield as an oil.

NMR: (200 MHz, DMSO-D6)δ: 2.10 (m, 1H (cis)); 2.66 (m, 1H (cis)); trans obscured by DMSO; 3.70 (m, 2H); 4.15 (q+t, 1H); 4.72 (m, 1H (cis)); merging with: 4.83 (m, 1H (trans)); 7.13 (AB, 2H); 7.72 (AB, 2H).

MS: $CI^+(M+NH_4^+)$=361.

REFERENCE EXAMPLE 5

5R, 3RS-5--Aminomethyl-3-(4-iodophenyl) dihydrofuran-2(3H)-one

To a stirred solution of 5R, 3RS-5-azidomethyl-3-(4-iodophenyl)dihydrofuran-2-one (Reference Example 4) (17.7 g, 52 mM) in dimethoxyethane (DME) (100 ml) at 50° C. under argon, was slowly added a solution of trimethylphosphite (7.74 g, 62.6 mM, 7.36 ml) in DME (20 ml). When effervescence had subsided, the mixture was heated under reflux for 2 hours. 6N Hydrochloric acid (1 1 ml, 66 mM) was added and reflux was continued for 18 hours. The solution was evaporated thoroughly and the residue was triturated with DME to give a thick precipitate which was filtered off, washed with DME and then with ether to give the title product. Yield (isolated)=6.61 g (36%).

NMR: (200 MHz, DMSO-D6)δ: 2.17 (m, 1H (cis)); 2.35 (m, partially obscured by DMSO); 2.69 (m, 1H) (cis)); 3.20 (m, 2H); 4.20 (t+q, 1H); 4.77 (m, 1H (cis)); 4.90, partially merged (m, 1H (trans)); 7.14 (2×d, 2H); 7.73 (2×d, 2H); 8.33 (broad s, 3H). Cis:trans=2:1.

MS: $EI^+M^+$=317.
Elemental Analysis:
  Calculated for $C_{11}H_{12}INO_2$: C, 37.4; H, 3.7; N, 4.0.
  Found: C, 37.6; H, 3.8; N, 4.0.

REFERENCE EXAMPLE 6

5R. 3RS-5-Acetamidomethyl-3-(4-iodophenyl) dihydrofuran-2(3H)-one 5R, 3RS-5-Aminomethyl-3-(4-iodophenyl)dihydrofuran-2-one (isolated solid plus filtrate residue from Reference example 5) (total 50 mM nominal) was taken into a mixture of THF (100 ml)/water (25 ml) and adjusted to pH10 with aqueous sodium hydroxide while cooling to maintain the temperature at ambient. Acetic anhydride (10.2 g, 0.1 M, 9.4 ml) was added dropwise. After complete addition, the mixture was stirred for 30 minutes at ambient temperature. The mixture was extracted with ethyl acetate and the organic phase was washed with dilute hydrochloric acid, saturated NaHCO$_3$ and saturated NaCl. It was dried (over MgSO$_4$) and evaporated to give a crystalline mass. The product was isolated by MPLC (Merck 9385 silica, using a mixture of 5% methanol/dichloromethane as eluant) and triturated with ether to give the title product as a pure isomer mixture (cis:trans=2:1 by NMR). Yield=9.65 g (54% over 2 stages).

NMR:(200 MHz, DMSO-D6)δ: 1.83 (s, 3H); 1.98 (m, 1H (cis)); 2.41 (m, partially obscured by DMSO, trans); 2.60 (m, 1H (cis)); 3.39 (m, 2H); 4.09 (m, 1H); 4.59 (m, 1H); 7.10 (AB, 2H); 7.71 (AB, 2H); 8.26 (broad m, 1H).

MS: CI$^+$, (M+H)$^+$=360.

Elemental Analysis:
Calculated for C$_{13}$H$_{14}$INO$_3$: C, 43.5; H, 3.9; N, 3.9
Found: C, 43.7; H, 4.0; N, 3.9.

REFERENCE EXAMPLE 7

5R, 3RS-5-Acetamidomethyl-3-(4-trimethyltinphenyl)dihydrofuran-2(3H)-one

To a stirred suspension of 5R, 3RS-5-acetamidomethyl-3-(4-iodophenyl)dihydrofuran-2(3H)-one (Reference Example 6) (2.80g, 7.89 mM) in dioxan (35 ml degassed under argon) was added hexamethyldistannane (2.71g, 8.27 mM) followed by Pd(PPh$_3$)Cl$_2$ (0.24 g, 0.34 mM). The flask was re-inerted with argon and the reaction mixture was stirred at 95–100° C. for 3 hours after which the reaction was judged complete by TLC. The solution was filtered through a pad of Celite and evaporated to a dark oil. The title product was isolated as an oil by MPLC (Merck 9385 silica, using as eluant a mixture of dichloromethane/methanol increasing in polarity from 0% to 2% methanol). Yield=1.79 g (57%).

NMR (200MHz, DMSO-D6)δ: 0.18 (s,9H),1.75 (s, 3H), 1.9 (m, 1H(cis)), 2.3(m, 1H(trans)), 2.5 (m, 1H(cis)), 3.3 (m, 2H), 3.9 (m, 1H), 4.45 (m, 1H), 7.1 (m, 2H) 7.35 (d, 2H), 8.05 (m, 1H).

MS: ESP+(M+H)=398, (M+NH$_4$)=415.

REFERENCE EXAMPLE 8

2,3-Dihydro-4-trifluoromethylsulfonyloxy-(6H)-pyran

LDA/THF (31.5 ml of 1.92M solution) was slowly added to a stirred solution of tetrahydro-4H-pyran-4-one (5.5 g) in THF (30ml) at −70° C., under argon. The mixture was stirred for 30 minutes at −70° C. and then a solution of N-phenyl triflimide (21.6 g) in THF (30 mls) was added. The mixture was allowed to warm to ambient temperature and stirred for 18 hours. The reaction mixture was evaporated and subjected to chromatography by MPLC on Alumina (ICN, N32–63, using as eluant a mixture of ethyl acetate (5%) and iso-hexane). The product was distilled by Kugelruhr (100° C./10 mm). Remaining traces of the triflimide reagent were removed by a second MPLC (Silica, using as eluant a mixture of ethyl acetate (5%) and iso-hexane) followed by a second Kugelruhr distillation, giving the title compound as a colourless oil in 40% yield (5.1 g), which was stored at −20° C.

NMR (300 MHzCDCl$_3$):δ: 2.24(m,2H), 3.90(m,2H), 4.25 (m,2H), 5.82(m,1H).

REFERENCE EXAMPLE 9

5R-acetamidomethyl-3-(4-trimethyltinphenyl)furan-(5H)-2-one

Anhydrous potassium carbonate (5.8 g, 42 mM) was added to a stirred solution of Reference Example 6 (1.51 g, 4.2 mM) and phenyl disulfide (1.05 g, 4.85 mM) in THF (30ml), and the mixture was stirred vigorously at ambient temperature for 18 hours. More potassium carbonate (2.9 g, 21 mM) and phenyl disulfide (1.575 g, 7.475 mM) were added and the stirred mixture was heated under reflux for 6hours. N,N'-dimethylpropyleneurea (5 ml) was added and reflux was continued for a further 18 hours after which the reaction was virtually complete (as judged by TLC). Excess 2N hydrochloric acid was carefully added and the mixture was extracted with ethyl acetate. The organic phase was washed with saturated sodium chloride solution, dried over anhydrous sodium sulfate and evaporated to give a gum. 5R-Acetamidomethyl-3-(4-iodophenyl)-3-phenylthio-dihydrofuran-(3H)-2-one was isolated by MPLC (Merck 9385 silica, 30×450mm column, eluted with ethyl acetate) as an amorphous foam. Yield=1.21 g (62%).

NMR (200MHz. DMSO-D6):δ: 1.80(s,3H), 2.51(m, partially obscured (DMSO)), 3.80(d of d,1H), 3.35(m, partially obscured (H2O)), 4.70(m,1H), 7.11(AB,2H), 7.31(m,5H), 6.69(AB,2H), 8.12(t,1H)

MS: ESP+ (M+H)=468.

A solution of KIO$_4$ (600 mg, 2.8 mM) in water (10 ml) was added to a stirred solution of 5R-acetamidomethyl-3-(4-iodophenyl)-3-phenylthio-dihydrofuran-(3H)-2-one (1.19 g, 2.55 mM) in methanol (10 ml). Some separation of starting material occurred and more methanol (20 ml) was added to give solution. The mixture was stirred at ambient temperature for 18 hours and then more KIO$_4$ (600 mg, 2.8 mM) was added. Stirring was continued for a further 3 days after which the reaction was complete (as judged by TLC). The solvent was evaporated and the residue was partitioned between water and ethyl acetate. The organic phase was separated, washed with a saturated sodium chloride solution, dried over anhydrous Na$_2$SO$_4$ and evaporated to give a crystalline solid. This was triturated with ether and recrystallized from acetonitrile to give 5R-acetamidomethyl-3-(4-iodophenyl)furan-(5H)-2-one. Yield=497 mg (55%).

NMR (200 MHzDMSO-D6)δ: 1.77(s,3H), 3.47(t,2H), 5.24(d oft,1H), 7.63(AB,2H), 7.82(AB,2H), 8.01(d,1H), 8.15(t, 1H).

MS: ESP+ (M+H)=358.

Elemental analysis:
Calculated for C$_{13}$H$_{12}$INO$_3$: C, 43.7; H, 3.4; N, 3.9.
Found: C, 43.7; H, 3.3; N, 3.9.

5R-acetamidomethyl-3-(4-iodophenyl)furan-(5H)-2-one (1.61 g, 4.50 mmol) was suspended in dioxan (degassed by the bubbling of argon) (28 ml) and the flask purged with argon. Hexamethylditin (1.56 g, 1.00 ml, 4.77 mmol) was added followed by bis(triphenylphosphine)palladium(II) chloride (0.158 g, 0.225 mmol) and the mixture was stirred at 95° C. for 2 hours. The mixture was then cooled, filtered through Celite and evaporated to an oil. This was purified by MPLC (using a mixture of MeOH/CH$_2$Cl$_2$ increasing in polarity from 0% MeOH to 2% MeOH as eluant) to give the title stannane. Yield=1.47 g (83%).

NMR (250 MHz, CDCl$_3$):δ: 0.30 (t, 9H), 1.93 (s, 3H), 3.63 (ddd, 1H), 3.75 (ddd, 1H), 5.11–5.19 (m, 1H), 5.95 (bd s, 1H), 7.54 (d, 2H), 7.78 (D, 2H).

MS: ESP+ (M+H)=396.

REFERENCE EXAMPLE 10

N-(pyrimid-2-yl)-1,2,5,6-tetrahydro-4-trifluoromethyl-sulfonyloxypyridine

To a stirred solution of N-(pyrimid-2-yl)-piperidin-4-one (0.177 g, 1.0 mmol) in tetrahydrofuran (5 ml) at −70° C.

under argon was added LDA (1.92M in THF) (0.57 ml, 1.1 mmol). The solution was stirred for 20 minutes, then a solution of N-phenyl-bis(trifluoromethane-sulfonimide) (0.382 g, 1.07 mmol) in THF (3 ml) was slowly added. The solution was stirred overnight with warming to ambient temperature. The solution was evaporated to dryness and purified by alumina MPLC [using a mixture of 5% ethyl acetate/hexane as eluant] to afford the title product. Yield 0.166 g (54%).

NMR (250 MHz, CDCl$_3$):δ: 2.55 (s, 2H), 4.10 (t 2H), 4.39 (m, 2H), 5.88 (s, 1H), 6.55 (t, 1H), 8.35 (d, 2H).

MS: ESP+(M+H)=310.

REFERENCE EXAMPLE 11

2,3-dihydro-4-trifluoromethylsulfonyloxy-(6H)-thiopyran

To a stirred solution of tetrahydrothiopyran4-one (5.8 g, 50 mmol) in tetrahydrofuran (50 ml) at −70° C. under argon was added LDA (1.92M in THF) (26 ml, 50 mmol). The solution was stirred for 20 minutes, then a solution of N-phenyl-bis(trifluoromethane-sulfonimide) (17.85 g, 50 mmol) in THF (30 ml) was slowly added. The solution was stirred overnight with warming to ambient temperature. The solution was evaporated to dryness and purified by alumina MPLC (using a mixture of 3% Ethyl acetate/hexane as eluant) to afford the title product. Yield=8.5 g (69%).

NMR (250 MHz, CDCl$_3$) 2.60 (m, 2H), 2.85 (m, 2H), 3.30 (m, 2H), 5.95 (m, 1H).

REFERENCE EXAMPLE 12 tert-Butyldimethylsilyloxyacetyl Chloride

Glycolic acid (5.0 g, 66 mmol) in pyridine (65 ml) was purged with argon and then treated with tert-butyldimethylsilyl trifluoromethanesulfonate (42 g, 36 ml, 158 mmol) at 0° C., and the mixture was stirred for 2.5 hours. The 2-phase mixture was separated and the upper phase diluted with diethyl ether. This solution was cooled to 0° C., washed briefly with 10% hydrochloric acid, dried (MgSO4) and evaporated to the disilyl material (18 g, 97%). The disilyl material (3.48 g, 12.4 mmol) in dichloromethane (30 ml) at 0° C. was treated with DMF (6 drops) followed by oxalyl chloride (1.84 g, 1.30 ml, 14.50 mmol). After stirring for 3.5 hours, the solution was evaporated and the crude material purified by bulb-to-bulb distillation to afford the title product (60 mbar, 120° C.<T<150° C.) (0.95 g, 37%) contaminated with tert-butyldimethylsiloxane.

NMR (250 MHz, CDCl$_3$)δ: 0.1 (s, 6H), 0.9 (s, 9H), 4.52 (s, 2H).

REFERENCE EXAMPLE 13

5R-acetamidomethyl-3-(4-{1,2,5,6-tetrahydropyrid-4-yl}phenyl)furan-(5H)-2-one tert-Butyl-1,2,5,6-tetrahydro-4-(trifluoromethylsulfonoyloxy)pyridine-1-carboxylate (1.36 g, 4.09 mmol), tris(dibenzylideneacetone)dipalladium(0) (0.181 g, 0.2 mmol), triphenyl arsine (0.245 g, 0.8 mmol) and lithium chloride (0.47 g, 11.1 mmol) were dissolved in degassed N-methyl-2-pyrrolidinone (55 ml) under argon. The stannane (Reference Example 9) (1.47 g, 3.72 mmol) in N-methyl-2-pyrrolidinone (14 ml) was added and the solution stirred at 40° C. for 75 hours. TLC then indicated complete reaction and the solution was treated with potassium fluoride (2M) (10 ml, 20 mmol) and stirred for 30 minutes. The mixture was then drowned into water (200 ml) and extracted with ethyl acetate (3×100 ml). The organic extracts were washed with water (2×100 ml), dried (MgSO$_4$) and evaporated to a residue. This was purified by MPLC (using a mixture of MeOH/CH$_2$Cl$_2$ increasing in polarity from 0% MeOH to 3% MeOH, and then Ethyl acetate as eluant) to afford the N-BOC tetrahydropyridyl furanone (0.82 g, 53%). The N-BOC tetrahydropyridyl furanone (3.67 g, 8.9 mmol) was refluxed in TFA (12 ml) for 2 minutes, and then evaporated to a yellow gum which was triturated with diethyl ether to give the TFA salt of the title product (2.75 g, 72%) as a powder.

NMR (250 MHz, DMSO-D6)δ: 1.73 (s, 3H), 2.69 (s, 2H), 3.37 (s, 2H), 3.45 (t, 2H), 3.80 (s, 2H), 5.23 (s, 1H), 6.28 (s, 1H), 7.56 (d, 2H), 7.83 (d, 2H), 7.96 (s, 1H), 8.19 (t, 1H), 8.90 (bd s, 1H).

EXAMPLE 1

5R, 3RS-5-Acetamidomethyl-3-(4-[1-tert-butoxycarbonyl-1,2,5,6-tetrahydropyrid-4-yl] phenyl)-dihydrofuran-2(3H)-one To a stirred solution of tert-butyl-1,2,5,6-tetrahydro-4-(trifluoromethylsulfonyloxy)-pyridine-1 -carboxylate [Synthesis, 993 (1991)] (0.92 g,2.78 mM) in N-methyl pyrrolidone (15 ml, degassed with helium) under argon, was added Pd$_2$(dba)$_3$ (0.116 g,0.13 mM), triphenylarsine (0.159 g,0.52 mM) and lithium chloride (0.32 g,7.59 mM). After stirring for 5 minutes at ambient temperature a solution of Refence Example 7 (1.00 g,2.53 mM) in NMP (5 ml) was added and the reaction mixture stirred at ambient temperature for 18 hours after which the reaction was complete (as judged by TLC). A 1.0M solution of aqueous potassium fluoride (2.0 ml) was added and the reaction mixture was stirred at ambient temperature for 30 minutes. Water was added and the product was extracted with ethyl acetate. The organic phase was separated and washed with water, saturated aqueous sodium chloride solution, dried over anhydrous magnesium sulfate and evaporated to an oil. The title product was isolated as an oil by MPLC (Merck 9385 silica, using as eluant a mixture of dichloromethane/methanol increasing in polarity from 0% to 3% methanol).Yield= 0.372 g (35%). The product was a pure mixture of cis(3S) and trans(3R) isomers by NMR in a 2:1 ratio.

NMR (200 MHz, DMSO-D6)δ: 1.45 (s,9H), 1.85 (s, 3H), 1.95 (m, 1H(cis)), 2.1(m, 1H(trans)), 2.45 (m, 2H), 2.6(m, 1H(cis)), 3.4 (m, 2H), 3.55 (t, 2H), 4.0 (m, 2H), 4.1 (m, 1H), 4.60(m, 1H), 6.15 (m, 1H), 7.25 (m, 2H) 7.40 (d, 2H), 8.20 (m, 1H).

MS: ESP+(M+H)=415, (M+NH$_4$)=432.

EXAMPLE 2

5R, 3RS-5-Acetamidomethyl-3-(4-[1,2,5,6-tetrahydropyrid-4-yl]phenyl)dihydrofuran-2(3H)-one Example 1 (0.35 g,0.75 mM) was dissolved in an excess of TFA (3 ml) and the solution stirred at ambient temperature for 1.5 hours. Ether (50 ml) was added, precipitating a sticky gum. The ether was decanted off and the gum solidified on trituration with ether. Upon filtration the solid once more became a gum so the TFA salt was dissolved in methanol (20 ml), evaporated and dried under high vacuum. Yield=0.28 g (87.1%).

NMR (200 MHz DMSO-D6+CD$_3$OD):δ: 1.88 (s, 3H), 1.92 (m, 1H(cis)), 2.0 (m, 1H(trans)), 2.4 (m, 2H), 2.65 (m, 1H(cis)), 3.25 (m, 2H), 3.45 (t, 2H), 3.7 (m, 2H), 4.1 (m, 1H), 4.60(m, 1H), 6.2 (m, 1H), 7.3 (m, 2H) 7.45 (d, 2H), 8.25 (m, 1H), 9.55 (bd.s, 1H).

MS: ESP+(M+H)=315.

EXAMPLE 3

5R, 3RS-5-Acetamidomethyl-3-(4-[1-methoxycarbonyl-1,2,5,6-tetrahydropyrid-4-yl]phenyl)dihydrofuran-2(3H)-one The trifluoroacetate salt of Example 2 (0.30 g,0.70 mM) and sodium bicarbonate (0.24 g,2.80 mM) were dissolved in a mixture of acetone and water (10 ml: 5 ml) at 0° C. Methyl chloroformate (59.5 μl, 0.77 mM) was added and the reaction allowed to rise to ambient temperature, after which the reaction was complete (as judged by TLC). Water was added and the product extracted with ethyl acetate. The organic extracts were washed with saturated aqueous sodium bicarbonate solution, saturated aqueous sodium chloride solution, dried over anhydrous magnesium sulfate and evaporated to a solid. This was dried at 50° C. under high vacuum to give the title product. Yield=215.6 mg (82.5%).

NMR (250 MHz, DMSO-D6): δ: 1.85 (s, 3H), 2.0 (m, 1H(cis)), 2.2(m, 1H(trans)), 2.35 (m, 2H), 2.6(m, 1H(cis)), 3.4 (m, 2H), 3.55 (t, 2H), 3.65 (s, 3H), 4.05 (m, 2H), 4.1 (m, 1H), 4.60(m, 1H), 6.15 (m, 1H), 7.25 (m, 2H) 7.40 (d, 2H), 8.18(m, 1H).

MS: ESP+(M+H)=373, (M+NH$_4$)=390.
Analysis:
Calculated for $C_{20}H_{24}N_2O_5$: C, 64.5; H, 6.5; N, 7.52.
Found: C, 63.0; H, 6.6; N, 6.9.
Calculated for 0.5 moles $H_2O$: C, 63.0; H, 6.6; N, 7.3.

EXAMPLE 4

5R,3RS-5-Acetamidomethyl-3-(4-[1-methylsulfonyl-1,2,5,6-tetrahydropyrid-4-yl]phenyl)dihydrofuran-2(3H)-one The trifluoroacetate salt of Example 2 (0.30 g,0.70 mM) was dissolved in dichloromethane and triethylamine (0.48 ml, 3.5 mM) added. The stirred solution was cooled to 0° C. and methanesulfonylchloride (59.6 μl, 0.77 mM) was added over 5 minutes and the reaction allowed to rise to ambient temperature. After I hour the reaction was complete (as judged by TLC). Water was added and the dichloromethane layer separated. The organic extracts were washed with saturated aqueous sodium chloride solution, dried over anhydrous magnesium sulfate and evaporated to a solid. The title product was isolated by MPLC (Merck 9385 silica, using as eluant a mixture of dichloromethane and methanol increasing in polarity from 0% to 2.5% methanol). This was dried at 50° C. under high vacuum. Yield=185.0 mg (67.4%).

NMR (300 MHz, DMSO-D6):δ: 1.92 (s, 3H), 2.0 (m, 1H(cis)), 2.4 (m, 1H(trans)), 2.6 (m, 2H), 2.65 (m, 1H(cis)), 2.9 (s, 3H), 3.25 (t, 2H), 3.4 (m, 2H (under water peak)), 3.8 (s, 2H), 4.1 (m, 1H), 4.6 (m, 1H), 6.15 (s, 1H), 7.25 (m, 2H) 7.40 (d, 2H), 8.2(m, 1H).

MS: ESP+(M+H)=393.
Analysis:
Calculated for $C_{19}H_{24}N_2O_5S$:C, 58.1; H, 6.16; N, 7.14; S, 8.17.
Found: C, 55.4; H, 5.9; N, 6.7; S, 6.8.
Calculated for 1.0 mole $H_2O$:C, 55.6; H, 6.4; N, 6.8; S, 7.9.

EXAMPLE 5

5R,3RS-5-Acetamidomethyl-3-(4-[1-hydroxyacetyl-1,2,5,6-tetrahydropyrid-4-yl]phenyl) dihydrofuran-2 (3H)-one The trifluoroacetate salt of Example 2 (0.30 g,0.70 mM) was dissolved in DMF (30 ml) and triethylamine (0.48 ml, 3.5 mM) added. To this stirred solution was added 4-dimethylaminopyridine (8.5 mg,0.07 mM), glycolic acid (79.9 mg, 1.05 mM) and 1-ethyl-3-(3-dimethylaminopropyl)carbodiimide (EDC) (0.201 g, 1.05 mM). The reaction mixture was stirred under argon for 5 hours after which hardly any reaction had occurred (as determined by HPLC). A further 0.75 equivalents each of glycolic acid and EDC were added and the reaction stirred for a further 36 hours. After this time HPLC indicated 30% starting material remaining and the reaction mixture was worked-up by adding water and extracting with ethyl acetate. The organic extracts were washed with saturated aqueous sodium chloride solution, dried over anhydrous magnesium sulfate and evaporated to a gum. The title product was isolated by MPLC (Merck 9385 silica, using as eluant acetone, followed by a mixture of dichloromethane and methanol (5%)) as a solid. This was dried at 40° C. under high vacuum. Yield= 36.0 mg (13.8%).

NMR (400 MHz, DMSO-D6):δ: 1.85 (s, 3H), 2.1 (m, 1H(cis)), 2.4 (m, 1H(trans)), 2.6 (m, 2H), 2.65 (m, 1H(cis)), 3.25 (t, 2H), 3.50&3.70 (2×t, 1H), 4.1 (m, 5H), 4.55 (d, 1H) 4.65 (m, 1H), 6.15 (d, 1H), 7.25 (m, 2H) 7.40 (d, 2H), 8.2(m, 1H).

MS: ESP+(M+H)=373.
Analysis:
Calculated for $C_{20}H_{24}N_2O_5$.C, 64.5; H, 6.5; N, 7.52.
Found : C, 61.8; H, 6.6; N, 6.5.
Calculated for 1.0 mole $H_2O$:C, 61.5; H, 6.7; N, 7.2.

EXAMPLE 6

5R-Acetamidomethyl-3-(4-{2,3-dihydro-6H-pyran-4-yl}phenyl)furan-(5H)-2-one

The triflate (Reference Example 8) (0.58 g, 2.50 mmol), tris(dibenzylideneacetone)dipalladium(0) (0.144 g, 0.125 mmol), triphenyl arsine (0.153 g, 0.50 mmol) and lithium chloride (0.286 g, 6.75 mmol) were dissolved in degassed NMP (33 ml). The stannane (Reference Example 9) (0.89 g, 2.25 mmol) in NMP (9 ml) was added and the solution stirred at 40° C. for 17 hours. TLC indicated incomplete reaction and more triflate (0.155 g, 0.67 mmol) was added. After a further 20 hours, the solution was treated with aqueous potassium fluoride solution (2M) (6.50 ml, 12.50 mmol) and stirred for 20 minutes. The mixture was then drowned into water (150 ml) and extracted with ethyl acetate (3×80 ml). The organic extracts were washed with water (2×100 ml), dried (MgSO$_4$) and evaporated to a residue. This was purified by MPLC (using as eluant a mixture of MeOH/CH$_2$Cl$_2$ increasing in polarity from 0% MeOH to 3% MeOH) to afford product which was triturated with diethyl ether to give the title product (0.301 g, 43%) as a powder.

NMR (250 MHz CDCl$_3$):δ: 1.94 (s, 3H), 2.53 (bd s, 2H), 3.64 (dt, 1H), 3.76 (dt, 1H), 3.94 (t, 2H), 4.34 (d, 2H), 5.19 (s, 1H), 6.06 (bd t, 1H), 6.20 (bd s, 1H), 7.43 (d, 2H), 7.55 (s, 1H), 7.80 (d, 2H).

MS: ESP+(M+H)=314.

EXAMPLE 7

5R-Acetamidomethyl-3-(4-{1-[pyrimid-2-yl]-1,2,5,6-tetrahydropyrid-4-yl}phenyl)-furan-(5H)-2-one The triflate (Reference Example 10) (0.344 g, 1.11 mmol), tris(dibenzylideneacetone)dipalladium(0) (0.051 g, 0.056 mmol), triphenyl arsine (0.068 g, 0.222 mmol) and lithium chloride 90.127 g, 3.00 mmol) were dissolved in degassed N-methyl-2-pyrrolidinone (NMP) (10 ml). The stannane (Reference Example 9) (0.399 g, 1.0 mmol) in NMP (4 ml) was added and the solution was stirred at 40° C. for 60 hours. The mixture was then drowned into water (150 ml) and extracted with ethyl acetate (3×80 ml). Aqueous potassium fluoride solution (2M) (2.78 ml, 5.55 mmol) was added to the combined organic extracts and stirring continued for 20 minutes. The organic layer was washed with water (2×100 ml), dried (MgSO$_4$) and evaporated to a residue. This was purified by MPLC (using as eluant a mixture of MeOH/CH$_2$Cl$_2$ increasing in polarity from 0% MeOH to 4% MeOH) to afford a product which was triturated with diethyl ether to give the title product (0.053 g, 14%) as a powder.

NMR (250 MHz CDCl$_3$):δ:1.94 (s, 3H), 2.60–2.68 (m, 2H), 3.62 (ddd, 1H), 3.77 (ddd, 1H), 4.09 (t, 2H), 4.42 (d, 1H), 4.47 (d, 1H), 5.14 (m, 1H), 5.75–5.84 (m, 1H), 6.25–6.80 (m, 1H), 6.51 (t, 1H), 7.46 (d, 2H), 7.53 (d, 1H), 7.82 (d, 2H), 8.35 (d, 2H).

MS: ESP+(M+H)=391.

EXAMPLE 8

5R-Acetamidomethyl-3-(4-{2,3-dihydro-6H-thiopyran-4-yl}phenyl)furan-(5H)-2-one

The triflate (Reference Example 11) (2.0 g, 8.10 mmol), tris(dibenzylideneacetone)dipalladium(0) (0.375 g, 0.41 mmol), triphenyl arsine (0.50 g, 1.64 mmol) and lithium chloride (1.04 g, 25.00 mmol) were dissolved in degassed N-methyl-2-pyrrolidinone (NMP) (20 ml). The stannane (Reference Example 9) (1.60 g, 4.10 mmol) in NMP (4 ml) was added and the solution was stirred at 40° C. for 48 hours. The solution was treated with aqueous potassium fluoride solution (2M) (8.00 ml, 16.00 mmol) and stirred for 35 minutes. The mixture was then partitioned between water (100 ml) and ethyl acetate (100 ml) and the organic layer washed with water (2×100 ml), filtered through Celite, dried (MgSO$_4$) and evaporated to a residue. This was purified by MPLC (using ethyl acetate as eluant) to afford a product which was triturated with diethyl ether to give the title product (0.23 g, 17%) as a powder.

NMR (250 MHz, CDCl$_3$):δ: 1.94 (s, 3H), 2.66–2.74 (m, 2H), 2.90 (dd, 2H), 3.23–3.39 (m, 2H), 3.62 (ddd, 1H), 3.76 (ddd, 1H), 5.11–5.20 (m, 1H), 5.80–5.90 (m, 1H), 6.23 (t, 1H), 7.38 (d, 2H), 7.53 (d, 1H), 7.79 (d, 2H).

EXAMPLE 9

5R-Acetamidomethyl-3-(4-{1-hydroxyacetyl-1,2,5,6-tetrahydropyrid-4-yl}phenyl)-furan-(5H)-2-one To a stirred solution of the TFA salt (Reference Example 13) (0.249 g, 0.58 mmol) in acetone:water (2:1) (12 ml) at 0° C. was added sodium hydrogen carbonate (0.196 g, 2.30 mmol) and the acid chloride (Reference Example 12) (0.362 g, 1.74 mmol). After 1.5 hours more acid chloride (0.184 g, 0.88 mmol) was added and stirring continued for 19 hours at ambient temperature. TLC indicated remaining amine and more acid chloride (0.120 g, 0.28 mmol) was added and stirring continued for a further 4 hours. The solution was diluted with water (15 ml), extracted with ethyl acetate (3×30 ml), dried and evaporated. The residue was purified by MPLC (using as eluant a mixture of MeOH/CH$_2$Cl$_2$ increasing in polarity from 0% MeOH to 4% MeOH) to afford the title product (0.065 g, 30%) as a solid.

NMR (250 MHz, CDCl$_3$):δ: 1.95 (s, 3H), 2.59 (s, 2H), 3.45–4.05 (m, 6H), 4.23 (d, 2H), 4.30 (d, 1H), 5.20 (s, 1H), 6.10 (d, 1H), 6.47 (s, 1H), 7.37–7.50 (m, 2H), 7.59 (s, 1H), 7.80 (d, 2H).

MS: ESP+(M+H)=371.

EXAMPLE 10

5R-Acetamidomethyl-3-(4-{1-benzyloxyacetyl-1,2,5,6-tetrahydropyrid-4-yl}phenyl)-furan-(5H)-2-one To a stirred solution of the TFA salt (Reference Example 13) (0.213 g, 0.50 mmol) in acetone:water (2:1) (10 ml) at 0° C. was added sodium hydrogen carbonate (0.168 g, 2.00 mmol) and benzyloxyacetyl chloride (0.185 g, 0.158 ml, 1.74 mmol). After 4 hours more acid chloride (0.040 ml) was added and stirring continued for 19 hours. The solution was diluted with water (10 ml), extracted with ethyl acetate (2×20 ml), dried and evaporated to a solid. This was purified by MPLC (using as eluant a mixture of MeOH/CH$_2$Cl$_2$ increasing in polarity from 0% MeOH to 3% MeOH) and then triturated with diethyl ether to afford the title product (0.068 g, 30%) as a solid.

NMR (250 MHz, CDCl$_3$):δ: 1.91 (s, 3H), 2.55 (bd s, 2H), 3.60–3.78 (m, 3H), 3.83 (t, 1H), 4.18 (bd s, 1H), 4.24 (d, 3H), 4.60 (s, 2H), 5.18 (bd s, 1H), 6.09 (bd d, 1H), 6.22 (bd s, 1H), 7.25–7.42 (m, 7H), 7.57 (d, 1H), 7.80 (d, 2H).

MS: ESP+(M+H)=461.

EXAMPLE 11

5R-Acetamidomethyl-3-(4-{1-acetoxyacetyl-1,2,5,6-tetrahydropyrid-4-yl}phenyl)furan-(5H)-2-one To a stirred solution of the TFA salt (Reference Example 13) (0.201 g, 0.47 mmol) in acetone:water (2:1) (10 ml) at 0° C. was added sodium hydrogen carbonate (0.159 g, 1.89 mmol) and acetoxyacetyl chloride (0.129 g, 0.101 ml, 0.94 mmol). After 4 hours more acetoxyacetyl chloride (0.025 ml) was added and stirring continued for 0.25 hours. The solution was extracted with ethyl acetate (2×20 ml), dried and evaporated to a yellow oil. This was purified by MPLC (using as eluant a mixture of MeOH/CH$_2$Cl$_2$ increasing in polarity from 0% MeOH to 3% MeOH) and then triturated with diethyl ether to afford the title product (0.073 g, 38%) as a crystalline solid.

NMR (250 MHz, CDCl$_3$): δ: 1.93 (s, 31H), 2.20 (s, 3H), 2.60 (bd s, 2H), 3.58–3.90 (m, 4H), 4.10 (bd s, 1H), 4.25 (bd s, 1H), 4.79 (d, 2H), 5.18 (bd s, 1H), 6.02–6.18 (m, 2H), 7.40 (d, 2H), 7.57 (d, 1H), 7.80 (d, 2H).

MS: ESP+(M+H)=413.

EXAMPLE 12

The following illustrate representative pharmaceutical dosage forms containing the compound of formula I, or a pharmaceutically-acceptable salt thereof (hereafter compound X), for therapeutic or prophylactic use in humans:

| (a) | Tablet I | mg/tablet |
|---|---|---|
| | Compound X | 100 |
| | Lactose Ph.Eur | 179 |
| | Croscarmellose sodium | 12 |
| | Polyvinylpyrrolidone | 6 |
| | Magnesium stearate | 3 |
| (b) | Tablet II | mg/tablet |
| | Compound X | 50 |
| | Lactose Ph.Eur | 229 |
| | Croscarmellose sodium | 12 |
| | Polyvinylpyrrolidone | 6 |
| | Magnesium stearate | 3 |

-continued

| | (c) | Tablet III | mg/tablet |
|---|---|---|---|
| | | Compound X | 1 |
| | | Lactose Ph.Eur | 92 |
| | | Croscarmellose sodium | 4 |
| | | Polyvinylpyrrolidone | 2 |
| | | Magnesium stearate | 1 |
| | (d) | Capsule | mg/capsule |
| | | Compound X | 10 |
| | | Lactose Ph.Eur | 389 |
| | | Croscarmellose sodium | 100 |
| | | Magnesium stearate | 1 |
| | (e) | Injection I | (50 mg/ml) |
| | | Compound X | 5.0% w/v |
| | | Isotonic aqueous solution | to 100% |

Buffers, pharmaceutically-acceptable cosolvents such as polyethylene glycol, polypropylene glycol, glycerol or ethanol or complexing agents such as hydroxy-propyl β cyclodextrin may be used to aid formulation.

Note

The above formulations may be obtained by conventional procedures well known in the pharmaceutical art. The tablets (a)–(c) may be enteric coated by conventional means, for example to provide a coating of cellulose acetate phthalate.

What is claimed is:

1. A compound of the formula (I):

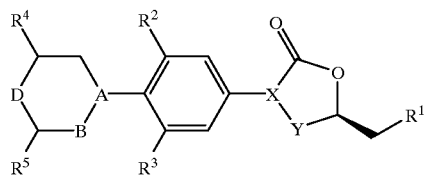

wherein $R^1$ is hydroxy or of the formula —NHC((=O)(1–4C)alkyl or —NHS(O)$_n$(1–4C)alkyl wherein n is 0, 1 or 2;

$R^2$ and $R^3$ are independently hydrogen or fluoro;

$R^4$ and $R^5$ are independently hydrogen or methyl >A—B— is of the formula >C=CH—, >CHCH$_2$—, or >C(OH)CH$_2$— (> represents two single bonds);

D is $NR^7$;

$R^7$ is hydrogen, cyano, 2-((1–4C)alkoxycarbonyl)ethenyl, 2-cyanoethenyl, 2-cyano-2-((1–4C)alkyl)ethenyl, 2-((1–4C)alkylaminocarbonyl)ethenyl, AR (as defined hereinbelow) or a tetrazole ring system (optionally mono-substituted in the 1- or 2-position of the tetrazole ring) wherein the tetrazole ring system is joined to the nitrogen in $NR^7$ by a ring carbon atom;

or $R^7$ is of the formula $R^{10}$CO—, $R^{10}$SO$_2$— or $R^{10}$CS— wherein $R^{10}$ is AR (as defined hereinbelow), cyclopentyl or cyclohexyl (wherein the last two-mentioned cycloalkyl rings are optionally mono— or disubstituted by substituents independently selected from (1–4C) alkyl (including geminal disubstitution), hydroxy, (1–4C)alkoxy, (1–4C)alkylthio, acetamido, (1–4C) alkanoyl, cyano and trifluoromethyl), (1–4C) alkoxycarbonyl, hydrogen, amino, trifluoromethyl, (1–4C)alkylamino, di((1–4C)alkyl)amino, 2,3-dihydro-5-oxothiazolo-[3,2-A]pyrimidin-6-yl, 2-(2-furyl)ethenyl, 2-(2-thienyl)ethenyl, 2-phenylethenyl (wherein the phenyl substituent is optionally substituted by up to three substituents independently selected from (1–4C)alkoxy, halo and cyano), 3,4-dihydropyran-2-yl, coumal-5-yl, 5-methoxy-4-oxopyran-2-yl, N-acetylpyrrolidin-2-yl, 5-oxo-tetrahydrofuran-2-yl, benzopyranone or (1–10C)alkyl {wherein (1–10C)alkyl is optionally substituted by hydroxy, cyano, halo, (1–10C)alkoxy, benzyloxy, trifluoromethyl, (1–4C)alkoxy-(1–4C)alkoxy, (1–4C) alkoxy-(1–4C)alkoxy-(1–4C)alkoxy, (1–6C)alkanoyl, (1–4C)alkoxycarbonyl, amino, (1–4C)alkylamino, di((1–4C)alkyl)amino, (1–6C)alkanoylamino, (1–4C) alkoxycarbonylamino, N-(1–4C)alkyl-N-(2–6C) alkanoylamino, (1–4C)alkylS(O)$_p$NH—, ((1–4C) alkylS(O)$_p$((1–4C)alkyl)NH—, fluoro(1–4C)alkylS(O)$_p$NH—, fluoro(1–4C)alkylS(O)$_p$((1–4C)alkyl)NH—, phosphono, (1–4C)alkoxy(hydroxy)phosphoryl, di-(1–4C)alkoxyphosphoryl, (1–4C)alkylS(O)$_q$—, phenylS(O)$_q$— (wherein the phenyl group is optionally substituted by up to three substituents independently selected from (1–4C)alkoxy, halo and cyano), or CY (as defined hereinbelow), wherein p is 1 or 2 and q is 0, 1 or 2};

or $R^{10}$ is of the formula $R^{11}$C(O)O(1–6C)alkyl wherein $R^{11}$ is an optionally substituted furan, optionally substituted pyrrole, optionally substituted pyrazole, optionally substituted imidazole, optionally substituted triazole, optionally substituted pyrimidine, optionally substituted optionally substituted pyridazine, optionally substituted pyridine, optionally substituted isoxazole, optionally substituted oxazole, optionally substituted isothiazole, optionally substituted thiazole, optionally substituted thiophene, optionally substituted phenyl, (1–4C)alkylamino, benzyloxy-(1–4C)alkyl or optionally substituted (1–10C)alkyl;

or $R^{10}$ is of the formula $R^{12}$O— wherein $R^{12}$ is optionally substituted (1–6C)alkyl;

or $R^7$ is of the formula $R^aOC(R^b)$=CH(C=O)—, $R^cC$(=O)C(=O)—, $R^dN$=C($R^e$)C(=O)— or $R^fNHC(R^8)$=CHC(=O)— wherein $R^a$ is (1–6C)alkyl, $R^b$ is hydrogen or (1–6C)alkyl, or $R^a$ and $R^b$ together form a (3–4C)alkylene chain, $R^c$ is hydrogen, (1–6C)alkyl, hydroxy(1–6C)alkyl, (1–6C)alkoxy(1–6C)alkyl, amino, (1–4C)alkylamino, di-(1–4C)alkylamino, (1–6C)alkoxy, (1–6C)alkoxy(1–6C)alkoxy,(1–6C)alkoxy, hydroxy(2–6C)alkoxy, (1–4C)alkylamino (2–6C)alkoxy, di-(1–4C)alkylamino(2–6C)alkoxy, $R^d$ is (1–6C)alkyl, hydroxy or (1–6C)alkoxy, $R^e$ is hydrogen or (1–6C)alkyl, $R^f$ is hydrogen, (1–6C)alkyl, optionally substituted phenyl or an optionally substituted is an optionally substituted furan, optionally substituted pyrrole, optionally substituted pyrazole, optionally substituted imidazole, optionally substituted triazole, optionally substituted pyrimidine, optionally substituted pyridazine, optionally substituted pyridine, optionally substituted isoxazole, optionally substituted oxazole, optionally substituted isothiazole, optionally substituted thiazole, or optionally substituted thiophene, and $R^8$ is hydrogen or (1–6C)alkyl;

or $R^7$ is of the formula $R^{14}CH(R^{13})$ (CH$_2$)$_m$— wherein m is 0 or 1, $R^{13}$ is fluoro, cyano, (1–4C)alkoxy, (1–4C) alkylsulfonyl, (1–4C)alkoxycarbonyl or hydroxy, (provided that when m is 0, $R^{13}$ is not fluoro or hydroxy) and $R^{14}$ is hydrogen or (1–4C)alkyl;

wherein AR is optionally substituted phenyl, optionally substituted phenyl(1–4C)alkyl, optionally substituted furan, optionally substituted pyrrole, optionally substituted pyrazole, optionally substituted imidazole, optionally substituted triazole, optionally substituted pyrimidine, optionally substituted pyridazine, optionally substituted pyridine, optionally substituted isoxazole, optionally substituted oxazole, optionally substituted isothiazole, optionally substituted thiazole, optionally substituted thiophene, optionally substituted naphthyl, optionally substituted indole, optionally substituted benzofuran, optionally substituted benzoimidazole, optionally substituted benzothiophene, optionally substituted benzoisothiazole, optionally substituted benzoxazole, optionally substituted benzisoxazole, optionally substituted pyridoimidazole, optionally substituted pyrimidoimidazole, optionally substituted quinoline, optionally substituted quinoxaline, optionally substituted quinazoline, optionally substituted phthalazine, optionally substituted cinnoline, or optionally substituted naphthyridine, in which the bicyclic heteroaryl ring systems may be linked via an atom in either of the rings comprising the bicyclic system, and wherein the mono- and bicyclic heteroaryl ring systems are linked via a ring carbon atom;

wherein CY is a 4-, 5- or 6-membered cycloalkyl ring, a 5- or 6-membered cycloalkenyl ring, naphthoxy, thiophen-2-yl, indol-1-yl, indol-3-yl, pyrimidin-2-ylthio, 1,4-benzodioxan-6-yl, sulfolan-3-yl, pyridin-2-yl; wherein any of the afore-mentioned ring systems in CY may be optionally substituted by up to three substituents independently selected from halo, (1–4C)alkyl (including geminal disubstitution when CY is a cycloalkyl or cycloalkenyl ring), acyl, oxo and nitro-(1–4C)alkyl;

>X—Y— is of the formula >C=CH— or >CHCH$_2$—;
and pharmaceutically-acceptable salts thereof.

2. A compound of the formula (I) as claimed in claim 1 wherein:

$R^1$ is hydroxy or of the formula —NHC(=O)(1–4C)alkyl or —NHS(O)$_n$(1–4C)alkyl wherein n is 0, 1 or 2;

$R^2$ and $R^3$ are independently hydrogen or fluoro;

$R^4$ and $R^5$ are independently hydrogen or methyl;

>A—B— is of the formula >C=CH—, >CHCH$_2$, or >C(OH)CH$_2$— (> represents two single bonds);

D is —NR$^7$;

wherein $R^7$ is hydrogen, 2-((1–4C)alkoxycarbonyl)ethenyl, 2-((1–4C)alkylaminocarbonyl)ethenyl or optionally substituted phenyl, optionally substituted phenyl(1–4C)alkyl, optionally substituted furan, optionally substituted pyrrole, optionally substituted pyrazole, optionally substituted imidazole, optionally substituted triazole, optionally substituted pyrimidine, optionally substituted pyridazine, optionally substituted pyridine, optionally substituted isoxazole, optionally substituted oxazole, optionally substituted isothiazole, optionally substituted thiazole, optionally substituted thiophene, optionally substituted naphthyl, optionally substituted indole, optionally substituted benzofuran, optionally substituted benzoimidazole, optionally substituted benzothiophene, optionally substituted optionally substituted benzoisothiazole, optionally substituted benzoxazole, optionally substituted benzisoxazole, optionally substituted pyridoimidazole, optionally substituted pyrimidoimidazole, optionally substituted quinoline, optionally substituted quinoxaline, optionally substituted quinazoline, optionally substituted phthalazine, optionally substituted cinnoline, or optionally substituted naphthyridine wherein the heteroaryl ring systems are joined to the nitrogen in NR$^7$ by a ring carbon atom;

or $R^7$ is of the formula $R^{10}$CO— or $R^{10}$SO$_2$— wherein $R^{10}$ is amino, (1–4C)alkylamino, di((1–4C)alkyl)amino, or (1–6C)alkyl {wherein (1–6C)alkyl is optionally substituted by hydroxy, cyano, (1–6C) alkoxy, benzyloxy, (1–6C)alkanoyl, amino, (1–4C)alkylamino, di-(1–4C) alkylamino, (1–6C)alkanoylamino, N-(1–4C)alkyl-N-(1–6C)alkanoylamino, (1–4C)alkylS(O)$_p$NH—, (1–4C)alkylS(O)$_p$((1–4C)alkyl)NH—, phosphono, (1–4C)alkoxy(hydroxy)phosphoryl, di-(1–4C)alkoxyphosphoryl, or (1–4C)alkylS(O)p wherein p is 1 or 2};

or $R^{10}$ is of the formula $R^{11}$C(O)O(1–6C)alkyl wherein $R^{11}$ is optionally substituted furan, optionally substituted pyrrole, optionally substituted pyrazole, optionally substituted imidazole, optionally substituted triazole, optionally substituted pyrimidine, optionally substituted pyridazine, optionally substituted pyridine, optionally substituted isoxazole, optionally substituted oxazole, optionally substituted isothiazole, optionally substituted thiazole, optionally substituted thiophene, optionally substituted phenyl or (1–6C)alkyl;

or $R^{10}$ is of the formula $R^{12}$O— wherein $R^{12}$ is optionally substituted (1–6C)alkyl; or $R^7$ is of the formula $R^a$OC(R$^b$)=CH(C=O)—, R$^c$C(=O)C(=O)—, R$^d$N=C(R$^e$)C(=O)— or R$^f$NHC(R$^g$)=CHC(=O)— wherein $R^a$ is (1–6C)alkyl, $R^b$ is hydrogen or (1–6C)alkyl or $R^a$ and $R^b$ together form a (3–4C)alkylene chain, $R^c$ is hydrogen, (1–6C)alkyl, hydroxy(1–6C)alkyl, (1–6C)alkoxy(1–6C)alkyl, amino, (1–4C)alkylamino, di-(1–4C)alkylamino, (1–6C) alkoxy, (1–6C)alkoxy(1–6C)alkoxy, hydroxy(2–6C)alkoxy, (1–4C)alkylamino(2–6C)alkoxy, di-(1–4C)alkylamino(2–6C)alkoxy, $R^d$ is (1–6C)alkyl, hydroxy or (1–6C)alkoxy, $R^e$ is hydrogen or (1–6C)alkyl, $R^f$ is (1–6C)alkyl, phenyl, furan, pyrrole, pyrazole, imidazole, triazole, pyrimidine, pyridazine, pyridine, isoxazole, oxazole, isothizole, thiazole, or thiophene, and $R^8$ is hydrogen or (1–6C)alkyl;

or $R^7$ is of the formula $R^{14}$CH(R$^{13}$) (CH$_2$)$_m$— wherein m is 0 or 1, $R^{13}$ is fluoro, cyano, (1–4C)alkoxy, (1–4C)alkylsulfonyl, (1–4C)alkoxycarbonyl or hydroxy; (provided that when m is 0, $R^{13}$ is not fluoro or hydroxy) and $R^{14}$ is hydrogen or (1–4C)alkyl;

>X—Y— is of the formula >C=CH— or >CHCH$_2$—;
and pharmaceutically-acceptable salts thereof.

3. A compound of the formula (I) as claimed in claim 1 wherein:

$R^1$ is of the formula —NHC(=O)(1–4C)alkyl;

$R^2$ and $R^3$ are independently hydrogen or fluoro;

$R^4$ and $R^5$ are independently hydrogen or methyl;

>A—B— is of the formula >C=CH— or >CHCH$_2$ (> represents two single bonds);

D is —NR$^7$;

wherein $R^7$ is hydrogen, 2-((1–4C)alkoxycarbonyl)ethenyl, 2-((1–4C)alkylaminocarbonyl)ethenyl, optionally substituted phenyl, optionally substituted phenyl(1–4C)alkyl, optionally substituted furan, optionally substituted pyrrole, optionally substituted pyrazole, optionally substituted imidazole, optionally substituted triazole, optionally substituted pyrimidine, optionally substituted pyridazine, optionally substituted pyridine, optionally substituted isoxazole, optionally substituted oxazole, optionally substituted isothiazole, optionally substituted thiazole, optionally substituted thiophene, optionally substituted naphthyl, optionally substituted indole, optionally substituted benzofuran, optionally substituted benzoimidazole, optionally substituted benzothiophene, optionally substituted optionally substituted benzoisothiazole, optionally substituted benzoxazole, optionally substituted benzisoxazole, optionally substituted pyridoimidazole, optionally substituted pyrimidoimidazole, optionally substituted quinoline, optionally substituted quinoxaline, optionally substituted quinazoline, optionally substituted phthalazine, optionally substituted cinnoline, or optionally substituted naphthyridine wherein the heteroaryl ring systems are joined to the nitrogen in $NR^7$ by a ring carbon atom;

or $R^7$ is of the formula $R^{10}CO-$ or $R^{10}SO_2-$;

wherein $R^{10}$ is amino, (1–4C)alkylamino, di((1–4C)alkyl) amino, or (1–6C)alkyl {wherein (1–6C)alkyl is optionally substituted by hydroxy, cyano, (1–6C)alkoxy, benzyloxy, (1–6C) alkanoyl, amino, (1–4C) alkylamino, di-(1–4C) alkylamino, (1–6C) alkanoylamino, N-(1–4C)alkyl-N-(1–6C) alkanoylamino, (1–4C)alkylS(O)$_p$NH—, (1–4C)alkylS (O)$_p$((1–4C)alkyl)NH—, phosphono, (1–4C)alkoxy (hydroxy)phosphoryl, di-(1–4C)alkoxyphosphoryl, or (1–4C)alkylS(O)p wherein p is 1 or 2};

or $R^{10}$ is of the formula $R^{11}C(O)O(1-6C)$alkyl wherein $R^{11}$ is optionally substituted furan, optionally substituted pyrrole, optionally substituted pyrazole, optionally substituted imidazole, optionally substituted triazole, optionally substituted pyrimidine, optionally substituted pyridazine, optionally substituted pyridine, optionally substituted isoxazole, optionally substituted oxazole, optionally substituted isothiazole, optionally substituted thiazole, optionally substituted thiophene, optionally substituted phenyl, or optionally substituted (1–6C)alkyl;

or $R^{10}$ is of the formula $R^{12}O-$ wherein $R^{12}$ is optionally substituted (1–6C)alkyl;

or $R^7$ is of the formula $R^aOC(R^b)=CH(C=O)-$, $R^cC(=O)C(=O)-$, $R^dN=C(R^e)C(=O)-$ or $R^fNHC(R^g)=CHC(=O)-$ wherein $R^a$ is (1–6C)alkyl, $R^b$ is hydrogen or (1–6C)alkyl or $R^a$ and $R^b$ together form a (3–4C)alkylene chain, $R^c$ is hydrogen, (1–6C)alkyl, hydroxy(1–6C)alkyl, (1–6C)alkoxy(1–6C)alkyl, amino, (1–4C)alkylamino, di-(1–4C)alkylamino, (1–6C) alkoxy, (1–6C)alkoxy(1–6C)alkoxy, hydroxy (2–6C)alkoxy, (1–4C)alkylamino(2–6C)alkoxy, di-(1–4C)alkylamino(2–6C)alkoxy, $R^d$ is (1–6C)alkyl, hydroxy or (1–6C)alkoxy, $R^e$ is hydrogen or (1–6C) alkyl, $R^f$ is (1–6C)alkyl, phenyl, furan, pyrrole, pyrazole, imidazole, triazole, pyrimidine, pyridazine, pyridine, isoxazole, oxazole, isothiazole, thiazole, or thiophene, and $R^g$ is hydrogen or (1–6C)alkyl;

or $R^7$ is of the formula $R^{14}CH(R^{13})(CH_2)_m-$ wherein m is 0 or 1, $R^{13}$ is fluoro, cyano, (1–4C)alkoxy, (1–4C) alkylsulfonyl, (1–4C)alkoxycarbonyl or hydroxy; provided that when m is 0, $R^{13}$ is not fluoro or hydroxy) and $R^{14}$ is hydrogen or (1–4C)alkyl;

>X—Y— is of the formula >C=CH— or >CHCH$_2$—;

and pharmaceutically-acceptable salts thereof.

4. A process for the preparation of a compound of the formula (I) as claimed in claim 1 which comprises:

(a) the deprotection of a compound of formula (II):

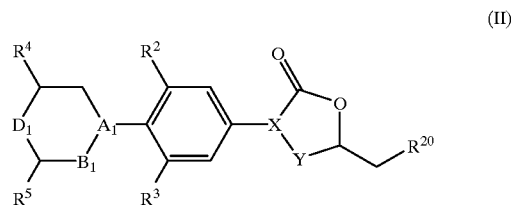

(II)

(b) the modification of a substituent in or the introduction of a substituent into another compound of the formula (I) or (II);

(c) when $R^{20}$ is of the formula —NHS(O)$_n$(1–4C)alkyl, wherein n is 1 or 2, the oxidation of a compound of the formula (I) or (II) wherein n is 0 or, when n is 2 the oxidation of a compound of the formula (I) or (II) wherein n is 1;

(d) when $R^{20}$ is of the formula —NHC(=O)(1–4C)alkyl or —NHS(O)$_n$(1–4C)alkyl, and >A$_1$—B$_1$— is >C=C—, >CHCH$_2$—, or protected >C(OH)CH$_2$— the reaction of a compound of the formula (III) with a compound of formula (IV):

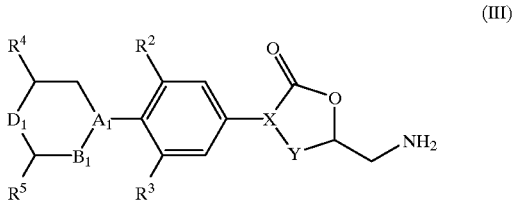

(III)

(IV)

(e) when $R^{20}$ is hydroxy and >X—Y— is >CHCH$_2$—:

the reaction of a compound of the formula (V) wherein >A$_1$—B$_1$— is >C=CH—, >CHCH$_2$— or protected >C(OH)CH$_2$— with a compound of formula (VI):

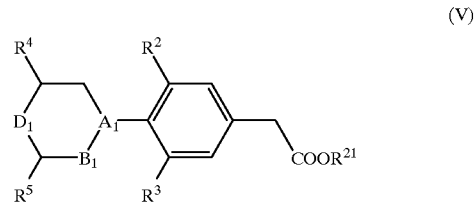

(V)

(VI)

or the reaction of a compound of the formula (V) with a compound of the formula (VII):

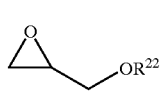
(VII)

(f) when >A$_1$—B$_1$— is >C=CH—, the reaction of a compound of the formula (VIII) with a compound of the formula (IX):

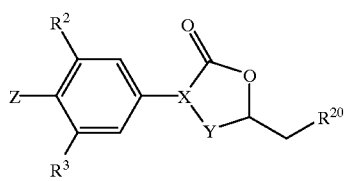
(VIII)

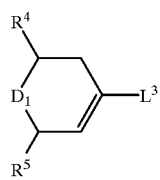
(IX)

(g) when >A$_1$—B$_1$— is >CHCH$_2$— and >X—Y— is >CHCH$_2$—, the catalytic hydrogenation of a compound of the formula (I) or (II) wherein >A$_1$—B$_1$— is >C=CH— and >X—Y is >CHCH$_2$—;

(h) when >A$_1$—B$_1$— is >C=CH— and >X—Y— is >CHCH$_2$—, the elimination of the elements of water, or HOCOR$^{23}$, or HOSO$_2$R$^{24}$ from a compound of the formula (X):

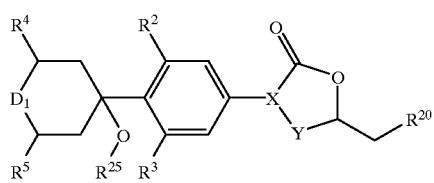
(X)

(i) when >A$_1$—B$_1$— is >C=CH— and >X—Y— is >CH=CH—, the elimination of the elements of water, HOCOR$^{23}$ or HOSO$_2$R$^{24}$ from a compound of the formula (X) wherein >X—Y— is >C(OR$^{25}$)—CH$_2$—;

(j) when >A$_1$—B$_1$— is >C=CH— and >X—Y— is >C=CH— the elimination of PhSOH from a compound of the formula (XI);

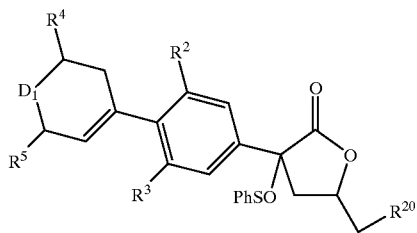
(XI)

(k) when D is NR$^7$ and R$^7$ is R$^{10}$CO—, R$^{10}$S(O)$_n$— or R$^{10}$CS—, the reaction of a compound of the formula (XII) wherein >A$_1$—B$_1$— is >C=CH—, >CHCH$_2$— or protected >C(OH)CH$_2$—, with a compound of the formula (XIII), (XIV) or (XV) respectively wherein n is 2:

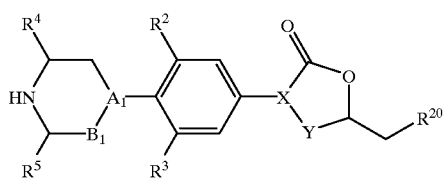
(XII)

R$^{10}$COL$^4$ (XIII)

R$^{10}$SO$_n$L$^{4a}$ (XIV)

R$^{10}$CSL$^{4b}$ (XV)

(l) when R$^{20}$ is of the formula —N(CO$_2$R$^{26}$)CO(1–4C) alkyl; from a compound of the formula (I) and (II) wherein R$^1$ or R$^{20}$ is hydroxy;

wherein R$^2$-R$^5$ and >X—Y— are as hereinabove defined; >A$_1$—B$_1$— is >A—B— or protected >C(OH)CH$_2$— and D$_1$ is D in which functional groups are optionally protected; R$^{19}$ is —C(=O)(1–4C)alkyl or —S(O)$_n$(1–4C)alkyl; R$^{20}$ is R$^1$ or protected R$^1$; R$^{21}$ is hydrogen or (1–6C)alkyl; R$^{22}$ is a protecting group; R$^{23}$ is (1–4C)alkyl; R$^{24}$ is an optionally substituted phenyl group; R$^{25}$ is hydrogen, (1–5C)alkanoyl or arylsulfonyl; R$^{26}$ is (1–4C)alkyl or benzyl; n is 0, 1 or 2 unless otherwise stated; L$^1$, L$^2$ and L$^{4a}$ are leaving groups, L4b is a leaving group (for example (1–4C)alkoxy), L$^3$ is an iodo or triflate leaving group, L$^4$ is hydroxy or a leaving group and Z is a trialkyltin residue, a boronate acid or ester residue or a zinc monohalide and thereafter if necessary any protecting groups are removed and a pharmaceutically-acceptable salt formed; and when an optically active form of a compound of the formula (I) is required, it may be obtained by carrying out one of the above procedures using an optically active starting material, or by resolution of a racemic form of the compound or intermediate using a standard procedure; and when a pure regioisomer of a compound of the formula (I) is required, it may be obtained by carrying out one of the above procedures using a pure regioisomer as a starting material, or by resolution of a mixture of the regioisomers or intermediates using a standard procedure.

5. A pharmaceutical composition which comprises a compound of the formula (I) or a pharmaceutically-acceptable salt thereof, as claimed in claim 1 and a pharmaceutically-acceptable diluent or carrier.

6. A method of treating a bacterial infection in a warm blooded animal in need of such treatment comprising administering to said animal an effective amount of a compound of claim 1.

7. A compound of formula (I):

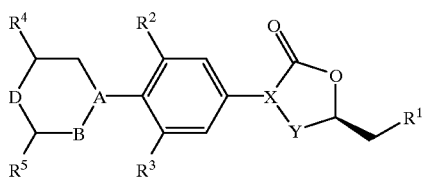

(I)

wherein $R^1$ is acetamido; >X—Y— is of the formula >C=CH—; both $R^2$ and $R^3$ are hydrogen; >A—B— is of the formula >C=CH—; $R^4$ and $R^5$ are hydrogen; D is of the formula —$NR^7$; $R^7$ is hydrogen or of the formula $R^{10}CO$—; $R^{10}$ is hydroxy(1–4C)alkyl, (1–4C)alkanoyloxy(1–4C)alkyl or (1–5C)alkoxy; or a pharmaceutically acceptable salt thereof.

8. A compound of formula (I)

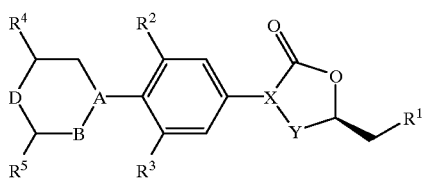

(I)

wherein $R^1$ is acetamido; >X—Y— is of the formula >C=CH—; one of $R^2$ and $R^3$ is hydrogen and the other is fluoro; >A—B— is of the formula >C=CH—; $R^4$ and $R^5$ are hydrogen; D is of the formula —$NR^7$; $R^7$ is hydrogen or of the formula $R^{10}CO$—; $R^{10}$ is hydroxy(1–4C)alkyl, (1–4C)alkanoyloxy(1–4C)alkyl or (1–5C)alkoxy; or a pharmaceutically acceptable salt thereof.

9. A pharmaceutical composition comprising a compound of formula (I):

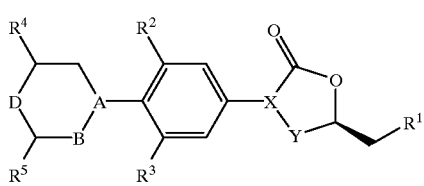

(I)

wherein $R^1$ is acetamido; >X—Y— is of the formula >C=CH—; both $R^2$ and $R^3$ are hydrogen; >A—B— is of the formula >C=CH—; $R^4$ and $R^5$ are hydrogen; D is of the formula —$NR^7$; $R^7$ is hydrogen or of the formula $R^{10}CO$—; $R^{10}$ is hydroxy(1–4C)alkyl, (1–4C)alkanoyloxy(1–4C)alkyl or (1–5C)alkoxy; or a pharmaceutically acceptable salt thereof, and a pharmaceutically acceptable diluent or carrier.

10. A pharmaceutical composition comprising a compound of formula (I)

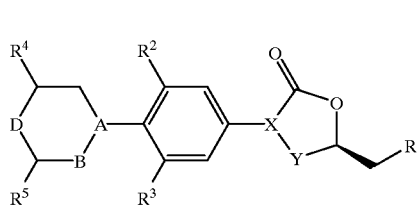

(I)

wherein $R^1$ is acetamido; >X—Y— is of the formula >C=CH—; one of $R^2$ and $R^3$ is hydrogen and the other is fluoro; >A—B— is of the formula >C=CH—; $R^4$ and $R^5$ are hydrogen; D is of the formula —$NR^7$; $R^7$ is hydrogen or of the formula $R^{10}$ CO—; $R^{10}$ is hydroxy(1–4C)alkyl, (1–4C)alkanoyloxy(1–4C)alkyl or (1–5C)alkoxy; or a pharmaceutically acceptable salt thereof, and a pharmaceutically acceptable diluent or carrier.

11. A method of treating a bacterial infection in a warm blooded animal in need of such treatment comprising administering to said animal an effective amount of a compound of formula (I):

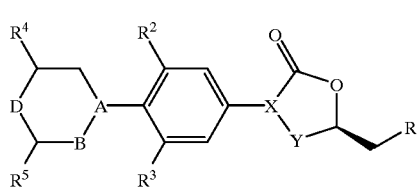

(I)

wherein $R^1$ is acetamido; >X—Y— is of the formula >C=CH—; both $R^2$ and $R^3$ are hydrogen; >A—B— is of the formula >C=CH—; $R^4$ and $R^5$ are hydrogen; D is of the formula —$NR^7$; $R^7$ is hydrogen or of the formula $R^{10}CO$—; $R^{10}$ is hydroxy(1–4C)alkyl, (1–4C)alkanoyloxy(1–4C)alkyl or (1–5C)alkoxy; or a pharmaceutically acceptable salt thereof.

12. A method of treating a bacterial infection in a warm blooded animal in need of such treatment comprising administering to said animal an effective amount of a compound of formula (I):

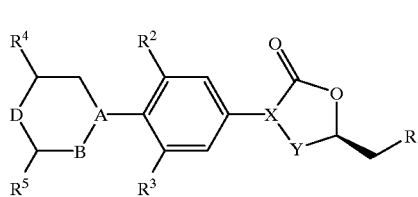

(I)

wherein $R^1$ is acetamido; >X—Y— is of the formula >C=CH—; one of $R^2$ and $R^3$ is hydrogen and the other is fluoro; >A—B— is of the formula >C=CH—; $R^4$ and $R^5$ are hydrogen; D is of the formula —$NR^7$; $R^7$ is hydrogen or of the formula $R^{10}CO$—; $R^{10}$ is hydroxy(1–4C)alkyl, (1–4C)alkanoyloxy(1–4C)alkyl or (1–5C)alkoxy; or a pharmaceutically acceptable salt thereof.

13. The compound 5R-acetamidomethyl-3-(4-[1-hydroxyacetyl-1,2,5,6-tetrahydropyrid-4-yl]phenyl)furan-2 (5H)-one, or a pharmaceutically acceptable salt thereof.

* * * * *